(12) United States Patent
Yamamoto et al.

(10) Patent No.: US 7,202,371 B2
(45) Date of Patent: Apr. 10, 2007

(54) CATALYTIC ASYMMETRIC EPOXIDATION

(75) Inventors: Hisashi Yamamoto, Chicago, IL (US); Arindrajit Basak, Chicago, IL (US); Wei Zhang, Chicago, IL (US)

(73) Assignees: The University of Chicago, Chicago, IL (US); Japan Science and Technology Agency (JP)

( * ) Notice: Subject to any disclaimer, the term of this patent is extended or adjusted under 35 U.S.C. 154(b) by 27 days.

(21) Appl. No.: 10/762,028

(22) Filed: Jan. 20, 2004

(65) Prior Publication Data

US 2005/0159607 A1    Jul. 21, 2005

(51) Int. Cl.
*C07D 301/19* (2006.01)
*C07D 301/12* (2006.01)

(52) U.S. Cl. .................................. 549/529; 549/531
(58) Field of Classification Search ................ 549/529, 549/531
See application file for complete search history.

(56) References Cited

U.S. PATENT DOCUMENTS

| 4,471,130 A | 9/1984 | Katsuki et al. |
| 4,900,847 A | 2/1990 | Hanson et al. |
| 5,602,267 A | 2/1997 | Zhao |
| 6,271,400 B2 | 8/2001 | Sharpless et al. |

FOREIGN PATENT DOCUMENTS

JP       2002-88046        3/2002

OTHER PUBLICATIONS

Michaelson et al, JACS, 99 (6), p. 1990-1992 (1977).*
Hoshino et al, JACS, vol. 122, p. 10452-10453 (2000).*
Bernardi, P. et al., "A General and Convenient Procedure for the Synthesis of N-Alkylarylamines and N-Alkylheteroarylamines by Electrophilic Amination of Cuprates with N-Alkylhydroxylamines," *J. Org. Chem.*, 1999, 64(2), 641-643.
Blum, S.A. et al., "Enantioselective Oxidation of Di-*tert*-Butyl Disulfide with a Vanadium Catalyst: Progress toward Mechanism Elucidation," *J. Org. Chem.* 2003, 68(1), 150-155.
Bolm, C. and Kühn, T., "Asymmetric Epoxidation of Allylic Alcohols Using Vanadium Complexes of (N)-Hydroxy-[2.2]paracyclophane-4-carboxylic Amides," *Synlett*, 2000, 6, 899-901.
Bolm, C. and Bienewald, F., "Asymmetric Sulfide Oxidation with Vanadium Catalysts and $H_2O_2$**," *Angew. Chem. Int. Ed. Engl.*, 1995, 34 (23/24), 2640-2642.
Brougham, P. et al. "Oxidation Reactions Using Magnesium Monoperphthalate: A Comparison with *m*-Chloroperoxybenzoic Acid," *Synthesis*, 1987, 1015-16.
Cavello, L. and Jacobsen, H., "Electronic Effects in (salen)Mn-Based Epoxidation Catalysts," *J. Org. Chem.*, 2003, 68(16), 6202-6207.
Cogan, D.A. et al., "Catalytic Asymmetric Oxidation of *tert*-Butyl Disulfide. Synthesis of *tert*-Butanesulfinamides, *tert*-Butyl Sulfoxides, and *tert*-Butanesulfinimines," *J. Am. Chem. Soc.*, 1998, 120(32), 8011-19.
Dittmer, D.C. et al., "A Tellurium Transposition Route to Allylic Alcohols: Overcoming Some Limitations of the Sharpless-Katsuki Asymmetric Epoxidation," *J. Org. Chem.*, 1993, 58(3), 718-731.
Galsbøl, F. et al., "The Preparation, Separation, and Characterization of the lel$_3$-and ob$_3$-Isomers of Tris(*trans*-1,2-cyclohexanediamine)rhodium(III) Complexes," *Acta. Chem. Scand.* 1972, 26(9), 3605-3611.
Gao, Y. et al., "Catalytic Asymmetric Epoxidation and Kinetic Resolution: Modified Procedures Including in Situ Derivatization," *J. Am. Chem. Soc.*, 1987, 109(19), 5765-5780.
Grundke, G. et al., "Optically Active N-Hydroxy-α-L-Amino Acid Methyl Esters: An Improved and Simplified Synthesis," *Synthesis*, 1987, 1115-1116.
Hajipour, A. R. and Pyne, S.G., "A Rapid and Efficient Synthesis of Oxaziridines and Diaryl Nitrones Using Oxone," *J. Chem. Research (S)*, 1992, 388.
Hartung, J. and Greb, M., "Transition metal-catalyzed oxidations of bishomoallylic alcohols," *Journal of Organometallic Chemistry* 2002, 661, 67-84.
Hirao, T., "Vanadium in Modern Organic Synthesis," *Chemical Reviews*, 1997, 97(8), 2707-2724.
Hoshino, Y. et al., "Design of Optically Active Hydroxamic Acids as Ligands in Vanadium-Catalyzed Asymmetric Epoxidation," *Bull. Chem. Soc. Jpn.*, 2000, 73, 1653-1658.
Hoshino, Y. and Yamamoto, H., "Novel α-Amino Acid-Based Hydroxamic Acid Ligands for Vanadium-Catalyzed Asymmetric Epoxidation of Allylic Alcohols," *J. Am. Chem. Soc.*, 2000, 122(42), 10452-53.
Itoh, T. et al., "Vanadium-Catalyzed Epoxidation of Cyclic Allylic Alcohols, Stereoselectivity and Stereocontrol Mechanism," *Journal of the American Chemical Society*, 1979, 101(1), 159-169.
Katsuki, T. and Sharpless, K.B., "The First Practical Method for Asymmetric Epoxidation," *J. Am. Chem. Soc.*, 1980, 102(18), 5974-5976.
Khlestkin, V.K. et al., "Intramolecular Cyclization of 1,2-Bis(N-alkoxy-N-nitrosoamino)alkanes: A Unique Route to 4,5-Dihydro-1,2,3-triazole 2-Oxides," *Synthesis*, 2000, 5, 681-690.
Larrow, J.F. et al., "A Practical Method for the Large-Scale Preparation of [N,N-Bis(3,5-di-*tert*-butylsalicylidene)-1,2-cyclohexanediaminato(2-)]manganese(III) Chloride, a Highly Enantioselective Epoxidation Catalyst," *J. Org. Chem.*, 1994, 59(7), 1939-1942.
Ligtenbarg, A.G.J. et al., "Catalytic oxidations by vanadium complexes," *Coordination Chemistry Reviews*, 2003, 237, 89-101.

(Continued)

*Primary Examiner*—Bernard Dentz
(74) *Attorney, Agent, or Firm*—Brinks Hofer Gilson & Lione

(57) ABSTRACT

The present invention relates to the synthesis of chiral epoxides via a catalytic asymmetric oxidation of olefins. Additionally, the methodology provides a method of asymmetrically oxidizing sulfides and phosphines. This asymmetric oxidation employs a catalyst system composed of a metal and a chiral bishydroxamic acid ligand, which, in the presence of a stoichiometric oxidation reagent, serves to asymmetrically oxidize a variety of substrates.

39 Claims, No Drawings

OTHER PUBLICATIONS

Liu, G. et al., "Catalytic Asymmetric Synthesis of *tert*-Butanesulfinamide. Application to the Asymmetric Synthesis of Amines," *J. Am. Chem. Soc.*, 1997, 119(41), 9913-9914.

Makita, N. et al., "Asymmetric Epoxidation of Homoallylic Alcohols and Application in a Concise Total Synthesis of (-)-α-Bisabolol and (-)-8-epi-α-Bisabolol**," *Angew. Chem. Int. Ed.*, 2003, 42(8), 941-943.

Mazhukin, D. G. et al., "Interaction of 1,2-Bishyroxylamines with 1,2-Dicarbonyl Compounds. Isolation and Properties of 2,3-Dihydropyrazine-1,4-Dioxides," Novosibirsk Institute of Organic Chemistry, Siberian Branch, Russian Academy of Sciences, translated from *Khimiya Geterotsiklicheskikh Soedinenii*, 1993, 4, 514-522.

Mazhukin, D. G. et al., "Organic Chemistry—Synthesis of aliphatic 1,2-bishydroxylamines from 1,3-dihydroxyimidazolidines. The crystal structure of 1,2-bishydroxylaminocycloalkanes," *Russian Chemical Bulletin*, 1993, 42(5), 851-857.

Mazhukin, D. G. et al., "Synthesis of 1,2-bis(methoxyamino)cycloalkanes from alicyclic 1,2-bis(hydroxyamines)." *Russian Chemical Bulletin*, 1996, 45(4), 925-929.

Mazhukin, D.G. et al., "Synthesis of Indeno[1,2-b]pyrazine *N*-Oxides by Reaction of Ninhydrin with 1,2-Bishydroxylamines," *Liebigs Ann. Chem.* 1994, 983-987.

Michaelson, R. C. et al., "Chiral Hydroxamic Acids as Ligands in the Vanadium Catalyzed Asymmetric Epoxidation of Allylic Alcohols by *tert*-Butyl Hydroperoxide," *Journal of the American Chemical Society*, 1997, 99(6), 1990-1992.

Mihelich, E.D. et al., "Vanadium-Catalyzed Epoxidations. 2. Highly Stereoselective Epoxidations of Acyclic Homoallylic Alcohols Predicted by a Detailed Transition-State Model," *J. Am. Chem. Soc.*, 1981, 103(25), 7690-92.

Murase, N. et al., "Chiral Vanadium-Based Catalysts for Asymmetric Epoxidation of Allylic Alcohols," *J. Org. Chem.*, 1999, 64(2), 338-339.

Okachi, T. et al., "Catalytic Enantioselective Epoxidation of Homoallylic Alcohols by Chiral Zirconium Complexes," *Org. Lett.*, 2003, 5(1), 85-87.

Stoner, E.J. et al., "Benzylation via Tandem Grignard Reaction—Iodontrimethylsilane (TMSI) Mediated Reduction," *Tetrahedron*, 1995, 51(41), 11043-11062.

Tikhonov, A.Y. et al., "Synthesis and Inhibitory Effect on Platelet Aggregation and Antihypertensive Activity of 1-Hydroxy-2,5-dihydro-1*H*-imidazole-2-carboxylic Acid 3-Oxides, 1,3-Dihydroxyimidazolidine-2-carboxylic Acids, and 1,4-Dihydroxy-2,3-piperazinediones," *Arch. Pharm. Pharm. Med. Chem.*, 1999, 332, 305-308.

Traber, B. et al., "Chiral Hydroxamic Acids as Ligands for the Vanadium Catalyzed Asymmetric Epoxidation of Allylic Alcohols," *Bull Korean Chem. Soc.*, 2001, 22(6), 547-548.

Wu, H.L. and Uang, B.J., "Asymmetric epoxidation of allylic alcohols catalyzed by new chiral vanadium(V), complexes," *Tetrahedron: Assymmetry*, 2002, 13, 2625-28.

Hoshino, Y. and Yamamoto, H., "Development of optically active hydroxamic acid coordinator: asymmetric epoxidation reactions of aryl alcohol," *Yuki Gosei Kagaku Kyokaishi* (*J. Synth. Org. Chem. Jpn.*), 2002, 60(5), 504-505.

Waldemar, A., et al., "Control of Enantioselectivity through a Hydrogen-bonded template in the vanadium(V)-catalyzed epoxidation of allylic alcohols by optically active hydroperoxides", Tetrahedron: Asymmetry, 14(10), pp. 1355-1361.

International Search report dated Apr. 8, 2005.

Written Opinion for PCT/US2005/000306 dated Apr. 8, 2005.

\* cited by examiner

CATALYTIC ASYMMETRIC EPOXIDATION

BACKGROUND OF THE INVENTION

Catalytic asymmetric epoxidations are extremely useful methods for synthesizing chiral compounds and consequently these types of reactions have broad applicability in the pharmaceutical industry. In the early 1980's Sharpless disclosed an effective method for accessing chiral epoxy alcohols, using a titanium-tartarate complex in the presence of a stoichiometric achiral oxidant. Although this process consistently provides high enantioselectivity, it has a number of disadvantages, which include the required use of molecular sieves, the sensitivity of the catalyst system to air and water, and an extensive and complicated work-up.

The catalytic asymmetric oxidation, disclosed herein, has one or more of the following advantages over previously used methods. Because the catalyst system is not water sensitive, molecular sieves are not required and an aqueous solution of an organic hydroperoxide can be used as the achiral oxidant. The catalyst system is not air sensitive the reactions are performed under aerobic conditions. Reactions can be easily worked up, which makes this system much more amenable to large-scale reactions. This methodology can also be applied to the catalytic asymmetric oxidation of phosphines and sulfides.

BRIEF SUMMARY OF THE INVENTION

The present invention relates to the synthesis of chiral epoxides via a catalytic asymmetric oxidation of olefins. Additionally, the methodology provides a method of asymmetrically oxidizing sulfides and phosphines. This asymmetric oxidation employs a catalyst system composed of a metal and a chiral bishydroxamic acid ligand, which, in the presence of a stoichiometric quantity of an oxidation reagent, serves to asymmetrically oxidize a variety of substrates.

DETAILED DESCRIPTION OF THE INVENTION

It is intended that the foregoing detailed description be regarded as illustrative rather than limiting, and that it be understood that it is the following claims, including all equivalents, that are intended to define the spirit and scope of this invention.

General

The present invention is directed to a catalytic asymmetric oxidation of a substrate. The substrate for this reaction is selected from the group consisting of alkenes, sulfides and phosphines. This methodology generally forms reacting an alkene, phosphine, or sulfide, an organic hydroperoxide, and catalytic amounts of a metal and a chiral bishydroxamic acid ligand, to provide a chiral oxidation product.

Abbreviations and Definitions

When describing the compounds, compositions, methods and processes of this invention, the following terms have the following meanings, unless otherwise indicated.

"Acid chloride" refers to a compound of the following formula:

where, R' is selected from the group consisting of alkyl, cycloalkyl, heterocyclyl, aryl, heteroaryl, and arylalkyl.

"Alkene" or "olefin" refers to an unsaturated hydrocarbon group which may be linear, cyclic or branched or a combination thereof. These groups have at leas 1 double bond, but can also include 2 or more double bonds. Possible substituents can be selected from the group consisting of include hydrogen, alkyl, cycloalkyl, hydroxy, alkoxy, amino, alkylamino, halogen, heterocyclyl, aryl, heteroaryl, arylalkyl, O-silyl, and halogen. Alkene groups with 2 to 20 carbon atoms are preferred. Alkene groups with 2 to 16 carbon atoms are more preferred. Examples of alkene groups include ethenyl, n-propenyl, isopropenyl, n-but-2-enyl, n-hex-3-enyl and the like.

"Alkoxy" refers to those alkyl groups, having from 1 to 10 carbon atoms, attached to the remainder of the molecule via an oxygen atom. Alkoxy groups with 1–8 carbon atoms are preferred. The alkyl portion of an alkoxy may be linear, cyclic, or branched or a combination thereof. Examples of alkoxy groups include methoxy, ethoxy, isopropoxy, butoxy, cyclopentyloxy, and the like. An alkoxy group can also be represented by the following formula: —OR', where R' is the "alkyl portion" of an alkoxy group.

"Alkyl" by itself or as part of another substituent refers to a hydrocarbon group which may be linear, cyclic, or branched or a combination thereof having from 1 to 10 carbon atoms (preferably 1 to 8 carbon atoms). Examples of alkyl groups include methyl, ethyl, n-propyl, isopropyl, n-butyl, t-butyl, isobutyl, sec-butyl, cyclohexyl, cyclopentyl, (cyclohexyl)methyl, cyclopropylmethyl and the like.

"Alkylamino" refers to those alkyl groups, having from 1 to 10 carbon atoms, attached to the remainder of the molecule via a nitrogen atom. Alkylamino groups with 1–8 carbon atoms are preferred. The alkyl portion of an alkylamino may be linear, cyclic, or branched or a combination thereof. Examples of alkylamino groups include methyl amine, ethyl amine, isopropyl amine, butyl amine, dimethyl amine, methyl, isopropyl amine and the like. An alkylamino group can also be represented by the following formulae: —NR'— or —NR'R", or —NHR', where R' and R" are alkyl.

"Aryl" refers to an aromatic hydrocarbon group having a single ring or multiple rings which are fused together or linked covalently with 5 to 14 carbon atoms (preferably 5 to 10 carbon atoms). Examples of aryl groups include phenyl, naphthalene-1-yl, naphthalene-2-yl, biphenyl, anthracene and the like.

"Arylalkyl" refers to an aryl group, attached to the remainder of the molecule via an alkyl group. Such groups may have single or multiple substituents on either the aryl ring or on the alkyl side chain. Examples include benzyl, phenylethyl, styryl, 2-(4-methylphenyl)ethyl, triphenylmethane, and 2-phenylpropyl.

"Asymmetric" refers to a molecule lacking all elements of symmetry. For example, the following carbon center is asymmetric:

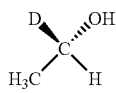

"Catalysis" or "catalyzed" refer to a process in which a relatively small amount of a foreign material increases the rate of a chemical reaction and is not itself consumed in the reaction.

"Catalytic amount" refers to a substoichiometric amount of the catalyst relative to a reactant.

"Catalytic asymmetric oxidation" refers to the transfer of an oxygen from an organic hydroperoxide to a pair of electrons, using a catalytic amount of a chiral bishydroxamic acid ligand and a metal, to produce an asymmetric product.

"Chiral" refers to a molecule or conformation which is not superimposable with its mirror image partner. The term "achiral" refers to molecule or conformation which is superimposable with its mirror image partner.

"Chiral catalyst" refers to a molecule or conformation, which is not superimposable with its mirror image partner and that increases the rate of a chemical reaction without itself being consumed. In an asymmetric catalytic reaction, the chiral catalyst will serve to catalyze the reaction, while also providing enantioselectivity.

"Chiral ligand" refers to a molecule or ion that surrounds a metal in a metal ion complex as a Lewis base, where the molecule is one which is not superimposable with its mirror image partner.

"Chiral oxidation product" refers to a molecule or compound which was transformed from a non-chiral to a chiral entity via the oxidation reaction disclosed herein.

"CHP" refers to cumene hydroperoxide.

"Complex" refers to a coordination compound formed by the union of one or more electronically rich molecules or atoms capable of independent existence with one or more electronically poor molecules or atoms, which is also capable of independent existence.

"Cyclic alkene" refers to alkenes or olefins, in which the unsaturated hydrocarbon group forms to members of a cycloalkyl or heterocyclyl moiety.

"Cycloalkyl" refers to hydrocarbon rings having from 3 to 12 carbon atoms and being fully saturated or having no more than one double bond between ring vertices (preferably 5 to 6 carbon atoms). Examples of cycloalkyl include cyclopropyl, cyclopentyl, cycloyhexyl and the like. "Cycloalkyl" is also meant to refer to bicyclic and polycyclic hydrocarbon rings such as, for example, bicyclo[2.2.1]heptane, bicyclo[2.2.2]octane, and the like.

"Dihydroxylamine hydrochloride" refers to compound having to hydroxylamine hydrochloride moieties. Hydroxylamine hydrochloride refers to a compound of the following formula:

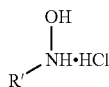

where R' is selected from the group consisting of alkyl, cycloalkyl, heterocyclyl, aryl, heteroaryl, and arylalkyl.

"Enantiomer" refers to one of a pair of molecular species that are mirror images of each other and not superposable.

"Enantiomerically enriched" refers to a mixture of enantiomers, in which one of the enantiomers has been selectively created in preference over the other enantiomer. Thus an "enantiomerically enriched" product will have an enantiomeric excess (i.e., % ee), in which one enantiomer is present in a larger amount than the other. To put it another way, "enantiomerically enriched" refers to having an enantiomer excess of more than 0 but less than 100%. "Enantiomeric excess" is equal to 100 times the mole fraction of the major enantiomer minus the more fraction of the minor enantiomer. In a mixture of a pure enantiomer (R or S) and a racemate, ee is the percent excess of the enantiomer over the racemate.

"Enantioselective" refers to a process which favors production of one of the two possible enantiomers of a reaction product. For example, a chemical reaction would be enantioselective if it produces the two enantiomers of a chiral product in unequal amounts. Such a reaction is said to exhibit enantioselectivity.

"Halo" or "halogen", by itself or as part of a substituent refers to a chlorine, bromine, iodine, or fluorine atom. Additionally, terms such as "Haloalkyl" refer to a monohaloalkyl or polyhaloalkyl group, most typically substituted with from 1–3 halogen atoms. Examples include 1-chloroethyl, 3-bromopropyl, trifluoromethyl and the like.

"Heteroatom" refers to an atom other than carbon. Examples include nitrogen, oxygen, sulfur, phosphorus and the like.

"Heterocyclyl" refers to a saturated or unsaturated non-aromatic group containing at least one heteroatom and having 3 to 10 members (preferably 3 to 7 carbon atoms). "Heteroaryl group" refers to an aromatic group containing at least one heteroatom and having 3 to 10 members (preferably 3 to 7 carbon atoms). Each heterocyclyl and heteroaryl can be attached at any available ring carbon or heteroatom. Each heterocyclyl may have one or more rings. When multiple rings are present in a heterocyclyl, they can be fused together or linked covalently. Each heteroaryl may have one or more rings. When multiple rings are present in a heteroaryl, they can be fused. Each heterocyclyl and hetroaryl can be fused to a cyclyl, heterocyclyl, heteroaryl, or aryl group. Each heterocyclyl and heteroaryl must contain at least one heteroatom (typically 1 to 5 heteroatoms) selected from nitrogen, oxygen or sulfur. Preferably, these groups contain 0–3 nitrogen atoms and 0–1 oxygen atoms. Examples of saturated and unsaturated heterocyclyl groups include pyrrolidine, imidazolidine, pyrazolidine, piperidine, 1,4-dioxane, morpholine, piperazine, 3-pyrroline and the like. Examples of heteroaryl groups include pyrrole, imidazole, oxazole, furan, triazole, tetrazole, oxadiazole, pyrazole, isoxazole, pyridine, pyrazine, pyridazine, pyrimidine, triazine, indole, benzofuran, benzimidazole, benzopyrazole, quinoline, isoquinoline, quinazoline, quinoxaline and the like. Heterocyclyl and heteroaryl groups can be unsubstituted or substituted. For substituted groups, the substitution may be on a carbon or heteroatom. For example, when the substitution is =O, the resulting group may have either a carbonyl (—C(O)—) or a N-oxide (—N(O)—).

"Inert atmosphere" refers to reaction conditions in which the mixture is covered with a layer of inert gas such as nitrogen or argon.

"Ligand" refers to the molecules or ions that surround the metal in a complex and serve as Lewis bases (i.e., electron pair donors).

"Metal" refers to elements located in Groups 5 and 6 of atomic number 23 to 74.

"Optically active 1,2-diammonium tartarate" refers to a compound of the following formula:

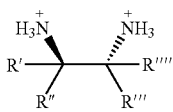

where, R', R", R'", and R"" are selected from the group consisting of hydrogen, alkyl, cycloalkyl, heterocyclyl, aryl, heteroaryl, and arylalkyl. The R" and R'" groups can also form members of the same ring, where the ring is a cycloalkyl or heterocyclyl group.

"Organic hydroperoxide" refers to an oxidant of the formula R'—O—O—H, where R' is selected from the group consisting of alkyl, cycloalkyl, and arylalkyl. Examples of organic hydroperoxides include tert-butyl hydroperoxide, α,α-dimethylheptyl hydroperoxide, bis-diisobutyl-2,5-dihydroperoxide, 1-methylcyclohexyl hydroperoxide, cumene hydroperoxide, cyclohexyl hydroperocide, and trityl hydroperoxide.

"Phospine" refers to a phosphorus atom possessing three subsituents. Substituents can be selected from the group consisting of alkyl, cycloalkyl, heterocyclyl, aryl, heteroaryl, and arylalkyl.

"Silyl protected dihydroxiamine" refers to a compound with two silyl protected hydroxylamines. Silyl hydroxylamine refers to a compound of the following formula:

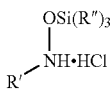

where, R' and R" are selected from the group consisting of alkyl, cycloalkyl, heterocyclyl, aryl, heteroaryl, and arylalkyl.

"Substituted" means that the moiety contains at least one, preferably 1 to 3 substituent(s). Suitable substituents include hydrogen, alkyl, cycloalkyl, alkoxy, alkylamino, alkylthio, halogen, heterocyclyl, aryl, heteroaryl, arylalkyl, or O-silyl. These substituents can optionally be further substituted with 1 to 3 substituents. Examples of substituted substituents include alkylamino, dialkylamino, alkylaryl, aralkyl, and the like.

"Sulfide" refers to a functional group, wherein a sulfur atom possesses two subsituents. A sulfide group can be represented as —S—, where possible subsituents can be selected from the group consisting of hydrogen, alkyl, cycloalkyl, heterocyclyl, aryl, heteroaryl, or arylalkyl.

"Sulfonyl" refers to a functional group, wherein a sulfur atom possesses four substituents, to of which are double bonded oxygens. A sulfonyl moiety may be represented as —S(O)$_2$—.

"TBHP" refers to tert-butyl hydroperoxide.

"*" refers to a center, molecule, or atom which is chiral.

All of the above terms (e.g., "alkyl," "aryl," "heteroaryl" etc.), in some embodiments, include both substituted and unsubstituted forms of the indicated groups. These groups may be substituted 1 to 10 times, as chemically allowed. Suitable substituents include alkyl, aryl, heteroaryl, heterocyclyl, halogen, alkoxy, oxygen, and nitrogen.

It is therefore intended that the foregoing detailed description be regarded as illustrative rather than limiting, and that it be understood that it is the following claims, including all equivalents, that are intended to define the spirit and scope of this invention.

Catalytic Asymmetric Oxidation

The asymmetric oxidation of the present invention can be represented as follows:

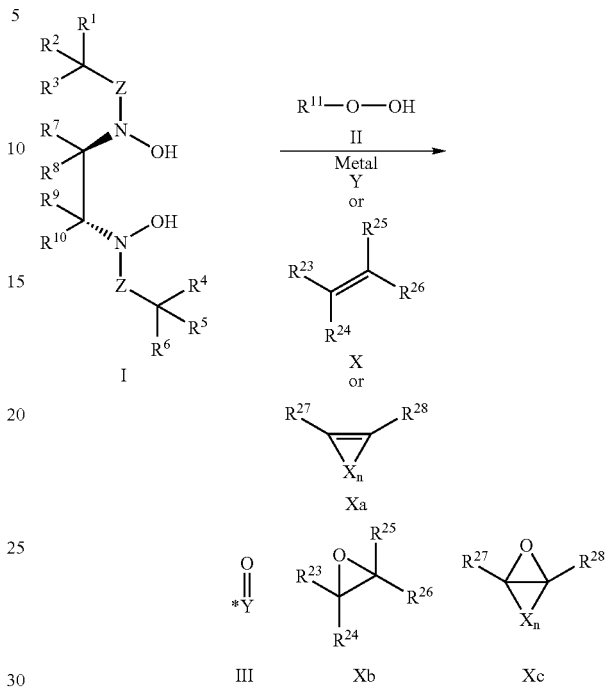

This reaction provides a method for the catalytic asymmetric oxidation of a substrate (Y), using catalytic amounts of a metal and a chiral bishydroxamic acid ligand (I), in the presence of an oxidation reagent. A number of potential substrates are shown (Y, X, and Xa). The resulting chiral oxidation products, in this example, are represented by compounds III, Xb, and Xc. The chiral bishydroxamic acid ligand (I), the oxidation reagent, the metal, the substrate, and the chrial oxidation product are all discussed individually below.

Chiral Bishydroxamic Acid Ligand

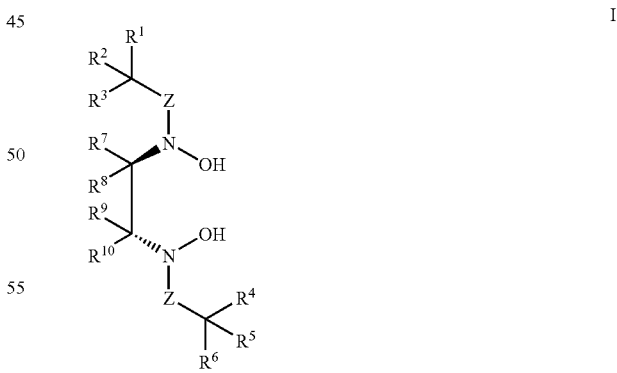

In one embodiment the chiral ligand, is represented by chiral bishydroxamic acid ligand I.

The -Z- linking groups, can each be independently selected from the group consisting of —C(O)— and —S(O)$_2$.

Substituents $R^1$, $R^2$, $R^3$, $R^4$, $R^5$, and $R^6$ are attached to the bishydroxamic backbone via the -Z- linking groups. Substituents $R^1$, $R^2$, $R^3$, $R^4$, $R^5$, and $R^6$ are each independently selected from the group consisting of hydrogen, alkyl, cycloalkyl, alkoxy, heterocyclyl, aryl, heteroaryl and arylalkyl.

Both of the hydroxamic acid nitrogens are also attached to an ethylene group, which is further substituted with $R^7$, $R^8$, $R^9$, and $R^{10}$. Substituents $R^7$, $R^8$, $R^9$, and $R^{10}$ are each independently selected from the group consisting of hydrogen, halogen, alkyl, cycloalkyl, alkoxy, alkylamino, heterocyclyl, aryl, heteroaryl and arylalkyl.

In one embodiment, substituents $R^1$, $R^2$, $R^3$, $R^4$, $R^5$, and $R^6$ are each independently selected, such that each is a different group or such that they are the same.

In another embodiment, substituents $R^1$, $R^2$, $R^3$, $R^4$, $R^5$, and $R^6$ are chosen such that: $R^1$ and $R^4$ are the same; $R^2$ and $R^5$ are the same; and/or $R^3$ and $R^6$ are the same.

In an additional embodiment, $R^1$, $R^2$, $R^4$, and $R^5$ may all be the same, while $R^3$ and $R^6$ are the same as each other, but different from $R^1$, $R^2$, $R^4$, and $R^5$.

In another embodiment, $R^1$, $R^2$, and $R^3$ can be chosen such that any two of these groups, together with the atom to which they are attached, form a ring.

In an additional embodiment, $R^4$, $R^5$, and $R^6$ can be chosen such that any two of these groups, together with the atom to which they are attached, form a ring.

For example, $R^1$ and $R^2$, along with the atom to which they are attached, can form a ring, where the ring is selected from the group consisting of cycloalkyl, heterocyclyl, or aryl. Likewise, $R^4$ and $R^5$, along with the atom to which they are attached, can form a ring, where the ring is selected from the group consisting of cycloalkyl, heterocyclyl, or aryl.

In one embodiment, the ring formed by $R^1$ and $R^2$, and the ring formed by $R^4$ and $R^5$ are identical and the rings are selected from the group consisting of cycloalkyl, hetercyclyl, and aryl.

The $R^7$, $R^8$, $R^9$, and $R^{10}$ substituents are each independently selected from the group consisting of hydrogen, alkyl, cycloalkyl, alkoxy, alkylamino, heterocyclyl, aryl, heteroaryl, and arylalkyl, such that each group is different or all of these groups are the same.

In a more preferred embodiment, the $R^7$ and $R^9$ substituents can be chosen such that these two groups are identical and the $R^8$ and $R^{10}$ substituents can be chosen such that these two groups are identical.

In one embodiment, $R^7$ and $R^9$, along with the atoms to which they are attached, form a ring, which is selected from the group consisting of cycloalkyl and heterocyclyl. The resulting chiral bishydroxamic acid ligand is compound Ia'.

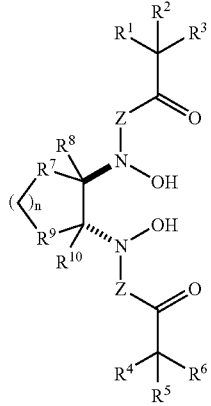

Ia'

In chiral bishydroxamic acid ligand Ia', $R^1$, $R^2$, $R^3$, $R^4$, $R^5$, $R^6$, $R^7$, $R^8$, $R^9$, $R^{10}$, and Z are defined as previously described.

The value of n can be 0, 1, 2, 3, or 4.

When $R^7$ and $R^9$, along with the atoms to which they are attached, form a ring, $R^8$ and $R^{10}$ can be the same or different.

In a preferred embodiment $R^1$, $R^2$, $R^4$, and $R^5$, are aryl groups; while $R^3$ and $R^6$ are hydrogen.

In a more preferred embodiment, $R^1$ and $R^2$ are identical aryl groups, and $R^4$ and $R^5$ are identical aryl groups, while $R^3$ and $R^6$ are hydrogen.

In a more preferred embodiment $R^1$, $R^2$, $R^4$, and $R^5$ are the same or identical aryl group, while $R^3$ and $R^6$ are hydrogen.

In another preferred embodiment, the chiral bishydroxamic acid ligand (I) is selected from the group consisting of:

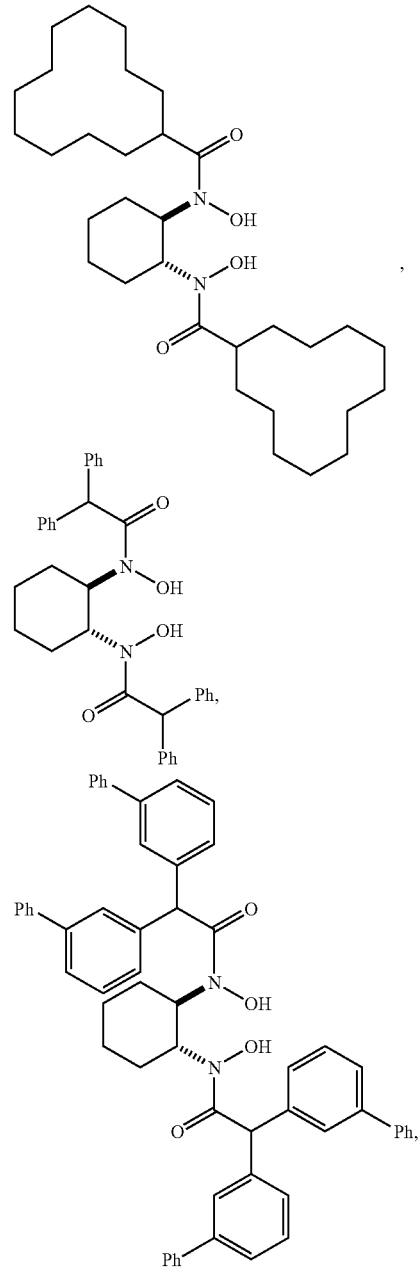

-continued
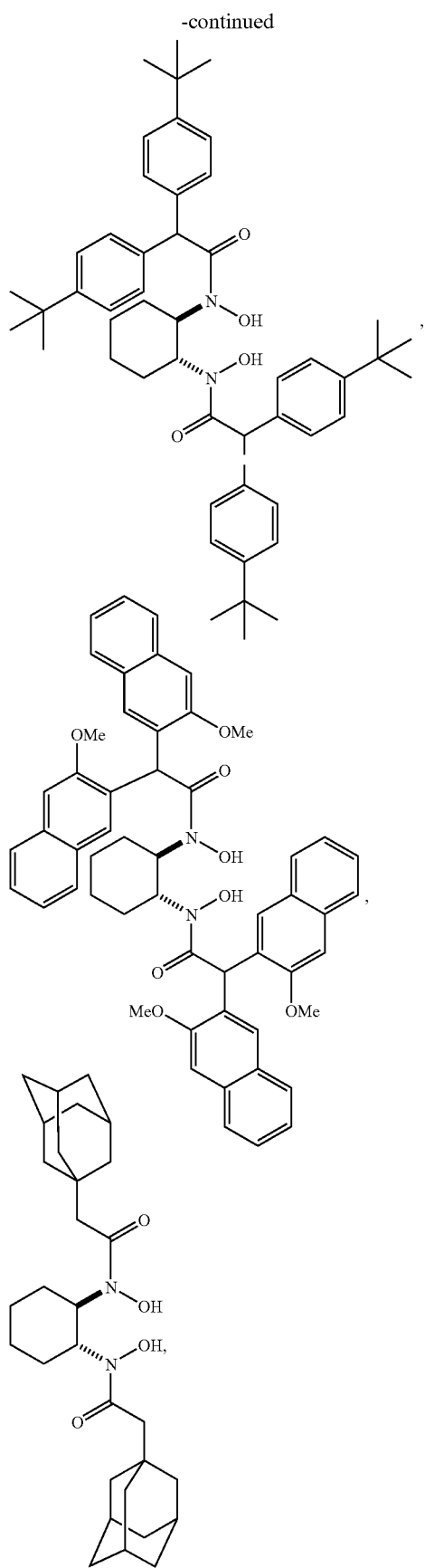
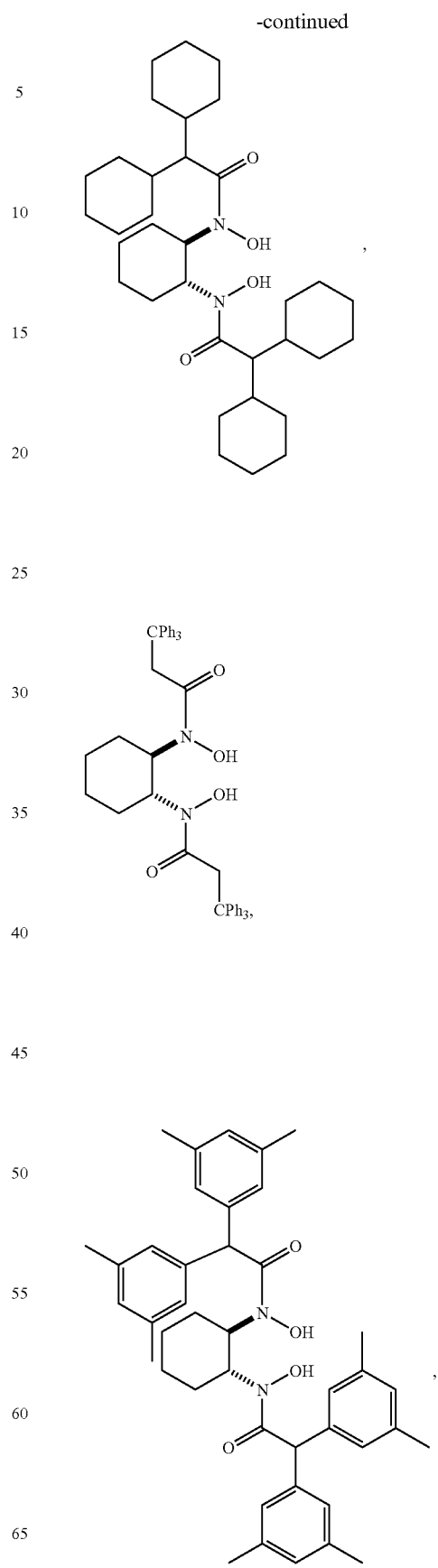

-continued

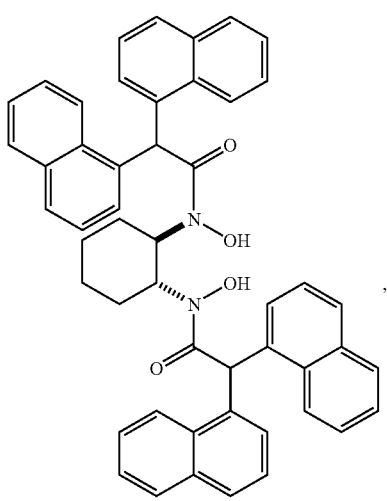
,

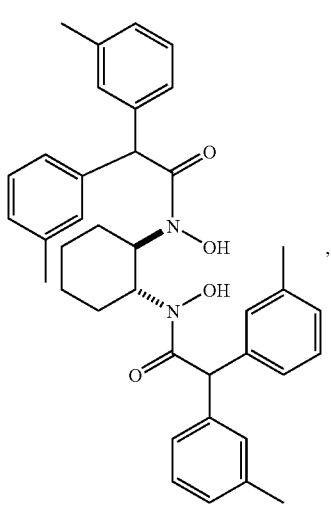
,

-continued

In one embodiment the chiral bishydroxamic acid ligand is prepared by condensing an optically active 1,2-diammonium tartarate (IV) with p-anisaldehyde to provide di-imine V. Next, the di-imine (V) is oxidized to produce dioxaziridine VI, which is subsequently hydrolyzed to generate dihydroxylamine hydrochloride VII. The dihydroxylamine hydrochloride (VII) is then silylated to provide silyl protected dihydroxiamine VIII.

Finally, the silyl protected dihydroxylamine (VIII) is condensed with an acid chloride to produce bishydroxamine acid IX.

-continued

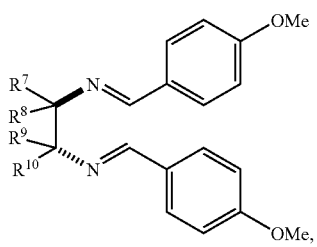
V

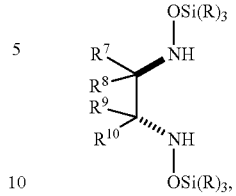
VIII

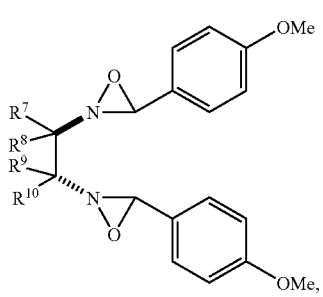
VI

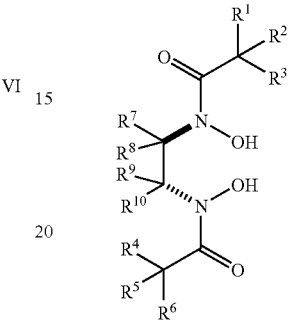
IX

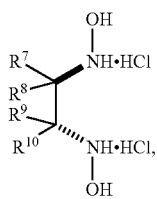
VII

In another embodiment, the chiral bishydroxamic acid ligand can be prepared by condensing an optically active 1,2-diammonium tartarate with p-anisaldehyde to provide a di-imine, which in turn is oxidized to produce a dioxadirizine. The dioxadirizine is then hydrolyzed to generate a dihydroxylamine hydrochloride. Subsequent, silylation of the dihydroxylamine hydrochloride provides a silyl protected dihydroxlamine, which is then condensed with an acid chloride to produce a chiral bishydroxamic acid ligand. The R group of $R_3SiX$ is typically an alkyl, while the X group can be selected from the group consisting of halo and triflate.

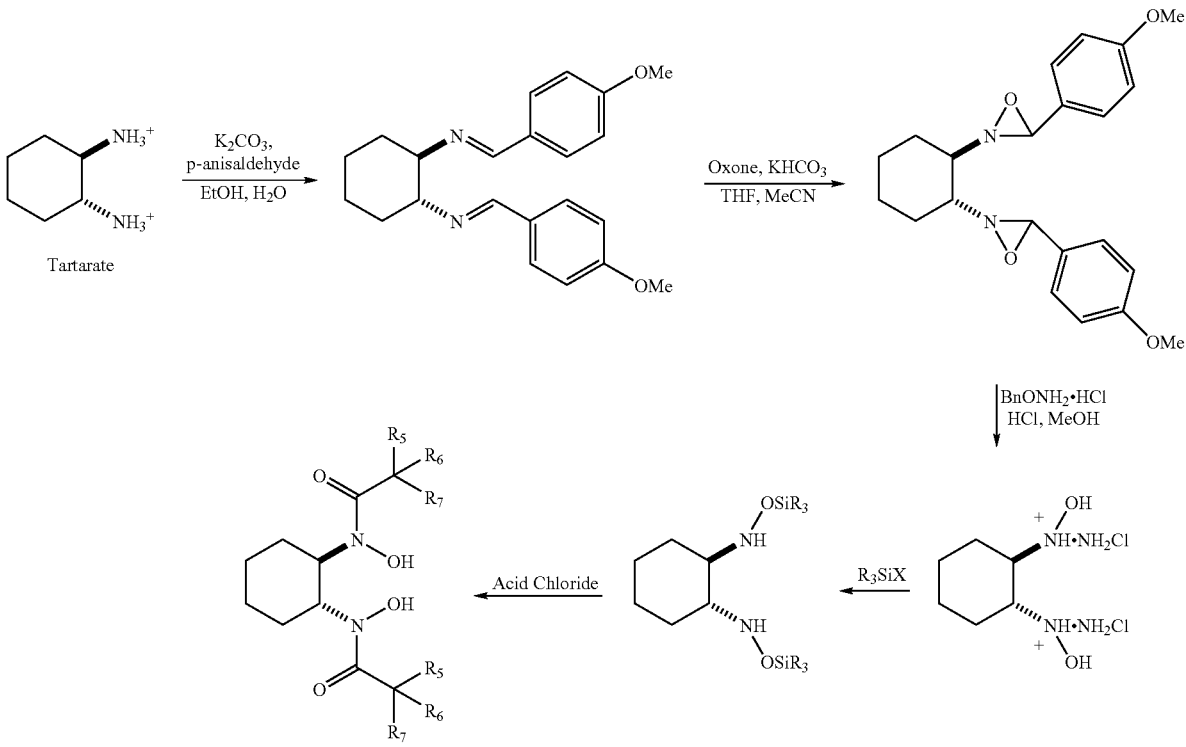

This synthetic route will provide chiral bishydroxamic acid ligands, wherein -Z- is —C(O)— and the ethylene backbone is part of a cyclohexane ring.

The $R^7$ and $R^9$ substituents, along with the atoms to which they are attached, form a cyclohexane ring, while $R^8$ and $R^{10}$ are hydrogen.

The identity of $R^1$, $R^2$, $R^3$, $R^4$, $R^5$, and $R^6$ depend on what acid chloride is condensed with the dihydroxylamine.

Examples of additional generic chiral bishydroxamic acid ligands include the following compounds:

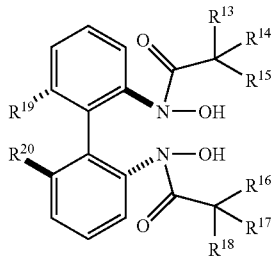

Ib'

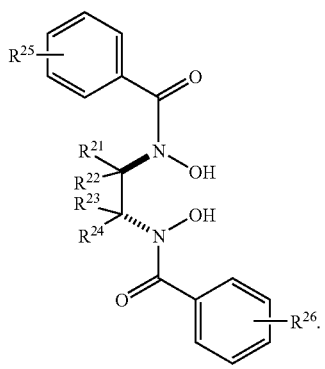

Ic'

With regard to compounds Ib' and Ic', $R^{13}$, $R^{14}$, $R^{15}$, $R^{16}$, $R^{17}$, and $R^{18}$ are each independently selected from the group consisting of hydrogen, alkyl, cycloalkyl, alkoxy, alkylamino, heterocyclyl, aryl, heteroaryl, and arylalkyl.

The $R^{19}$ and $R^{20}$ substituents are each independently selected from the group consisting of hydrogen, halogen, alkyl, cycloalkyl, alkoxy, alkylamino, heterocyclyl, aryl, heteroaryl, and arylalkyl.

The $R^{21}$, $R^{22}$, $R^{23}$, and $R^{24}$ substituents are each independently selected from the group consisting of hydrogen, alkyl, cycloalkyl, alkoxy, alkylamino, heterocyclyl, aryl, heteroaryl, and arylalkyl.

The $R^{25}$ and $R^{26}$ substituents are each independently selected from the group consisting of hydrogen, halogen, alkyl, cycloalkyl, alkoxy, alkylamino, heterocyclyl, aryl, heteroaryl, and arylalkyl.

It will be apparent to one skilled in the art that the two hydroxamic acids may be connected by more than two atoms. Compound Ib' would be an example of one such ligand. In compound Ib', the hydroxamic acids are separated by four carbon atoms which are members of a biphenyl backbone. Another example would be a bishydroxamic acid, where the hydroxamic acids are connected to a binaphthyl backbone. Furthermore, the atoms connecting the two hydroxamic acids can be atoms other than carbon, as long as the overall ligand is capable of imparting chirality to the catalytically active species.

In a more preferred embodiment, the chiral bishydroxamic acid ligand has the following structure (Id'):

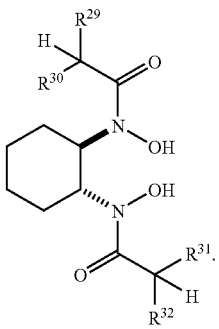

Id'

In chiral bishydroxamic acid ligand Id', $R^{29}$, $R^{30}$, $R^{31}$, and $R^{32}$ are each independently selected from the group consisting of alkyl, cycloalkyl, aryl, and arylalkyl. It is important to note that high enantiomeric excesses have resulted when the chiral bishydroxamic acid ligand has had this general structure.

Metal

In the present invention, the metal can be vanadium (IV) or vanadium (V). Additionally, the metal can be molybdenum (IV), or molybdenum (V). In a preferred embodiment, the metal is selected from the group consisting of VO(OPr$^i$)$_3$, VO(acac)$_2$, VO(OEt)$_3$, and MoO(acac)$_2$.

Oxidation Reagent

In the present invention the oxidation is performed by an oxidation reagent. In one embodiment, the oxidation reagent is an organic hydroperoxide. This compound can be represented by the following formula (II):

$$R^{11}\text{—O—OH} \qquad \text{II}$$

The $R^{11}$ substituent is selected from the group consisting of alkyl, cycloalkyl, and arylalkyl.

Examples of organic hydroperoxides include, but are not limited to, tert-butyl hydroperoxide, α,α-dimethylheptyl hydroperoxide, bis-diisobutyl-2,5-dihydroperoxide, 1-methylcyclohexyl hydroperoxide, cumene hydroperoxide, cyclohexyl hydroperoxide, and trityl hydroperoxide.

In a preferred embodiment the organic hydroperoxide is selected from the group consisting of tert-butyl hydroperoxide and cumene hydroperoxide.

In another embodiment the oxidation reagent is hydrogen peroxide.

Substrate

The present invention can be employed in conjunction with a variety of substrates. For example, the substrate can be selected from the group consisting of alkene, cyclic alkene, sulfide, or phosphine.

Additionally, each one of these substrates can be substituted or unsubstituted and can also be a member of a ring.

The present invention can be performed with an alkene substrate. Such an alkene can be represented by the following formula (X):

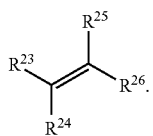
X

Substrate X, illustrates a potential alkene substrate where the $R^{23}$, $R^{24}$, $R^{25}$, and $R^{26}$ substituents are each independently selected from the group consisting of hydrogen, halogen, alkyl, cycloalkyl, alkoxy, alkylamino, heterocyclyl, aryl, heteroaryl, and arylalkyl.

This more detailed representation of an alkene substrate, illustrates application of the present invention to an alkene (X) substrate, wherein the oxidation is carried out using catalytic amounts of a chiral bishydroxamic acid (I) and a metal in the presence of an organic hydroperoxide. The asymmetric oxidation of the alkene provides a chiral oxidation product, in the form of a chiral epoxide (XII).

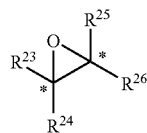
XII

The present invention can also be used in combination with cyclic alkenes, such as Xa.

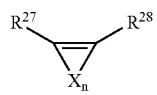
Xa

The substituents, $R^{27}$ and $R^{28}$, are each independently selected from the group consisting of hydrogen, alkyl, cycloalkyl, alkoxy, alkylamino, heterocyclyl, aryl, aralklyl, heteroaryl, halogen, and alkene.

The size of the ring is based on the value of n, which can be 1, 2, 3, 4, 5, 6, or 6. For example, when n is 1, the cyclic olefin is a 3-membered ring, with one X group. If n is 2, then the cyclic olefin is a 4-membered ring, with two X groups, and so on.

Each occurrence of X is independently selected from the group consisting of —$CR^{29}R^{30}$—, —$NR^{31}$—, and —O—, where $R^{29}$, $R^{30}$, and $R^{31}$ are each independently selected from the group consisting of hydrogen, alkyl, cycloalkyl, alkoxy, alkylamino, heterocyclyl, aryl, aralklyl, heteroaryl, halogen, and alkene.

In another embodiment, the substrate is selected from the group consisting of sulfide and phosphine.

It is important to note that one in the art would realize that, as with most organic reactions, this reaction can be performed with a variety of substrates. Furthermore, slight modifications of the substrate will often allow for optimization of the yield and the enantioselectivity.

Chiral Oxidation Product

In one embodiment, the chiral oxidation product can be represented as follows:

III where Y is a phosphine substrate or a sulfide substrate.

In another embodiment, the chiral oxidation product, as it is derived from alkene substrate X is shown below:

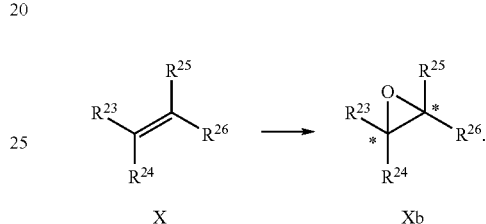
X        Xb

In another embodiment, the chiral oxidation product, as it is derived from alkene substrate Xa is shown below:

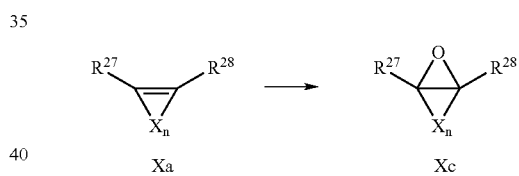
Xa        Xc

One skilled in the art will realize that the chiral oxidation product will vary depending on the substrate which is used. For example, when the substrate is a phosphine or sulfide, the chiral oxidation product will be a phosphine oxide or sulfoxide, respectively. In another example, when the substrate is an alkene, the chiral oxidation product will be an epoxide.

Reaction Conditions

The present invention is typically carried out in a solvent. Organic solvents are preferred. More preferably, the reaction is carried out in a solvent selected from the group consisting of methylene chloride, toluene, chloroform, and ethyl acetate.

The present invention can be performed at a variety of temperatures. In a preferred embodiment the reacting step is carried out at a temperature of about −20° C. to about 25° C.

Furthermore, the reaction disclosed herein is performed with various amounts of the chiral bishydroxamic acid ligand and the metal. In one preferred embodiment the reaction is carried out with about 0.001 to about 0.1 equivalents of the chiral bishydroxamic acid ligand. In another preferred embodiment, the reaction is carried out with about 0.005 to about 0.05 equivalents of the metal.

It is important to note that one skilled in the art would realize that optimization of the yield and the enantioselectivity can be achieved by altering the reaction conditions. For example, such optimization can include changing the solvent, the temperature of various stages of the reaction, the equivalents of the chiral bishydroxamic acid ligand, and the equivalents of the metal.

EXAMPLES

Scope of the Invention

The following tables further demonstrate the scope of the invention.

The ligands, referred to as Ia thru Io in the following tables, are shown below. These compounds can be made using the procedures provided in the synthetic examples section. It is important to note, that these ligands are illustrative of possible chiral bishydroxamic acid ligands. However, this list is in no way limiting.

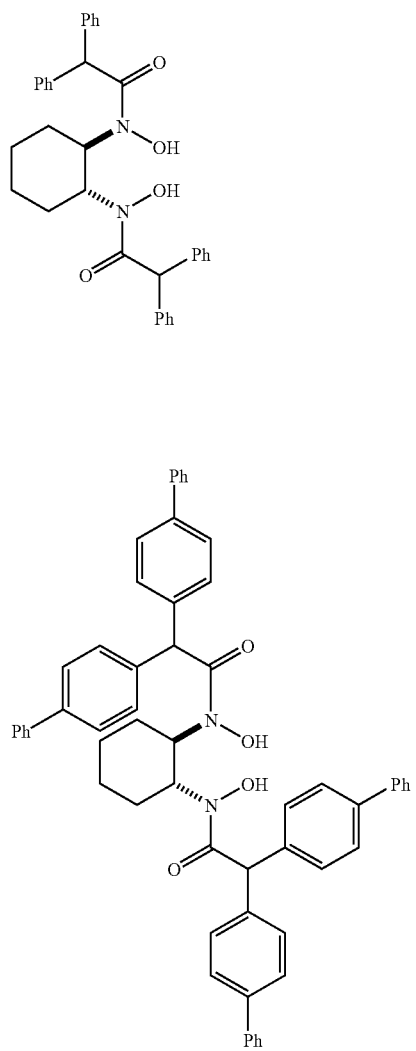

Ia

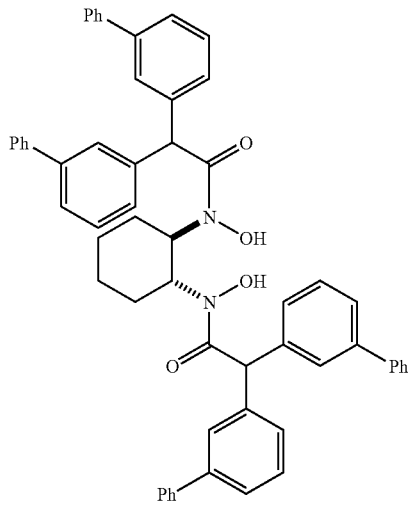

Ic

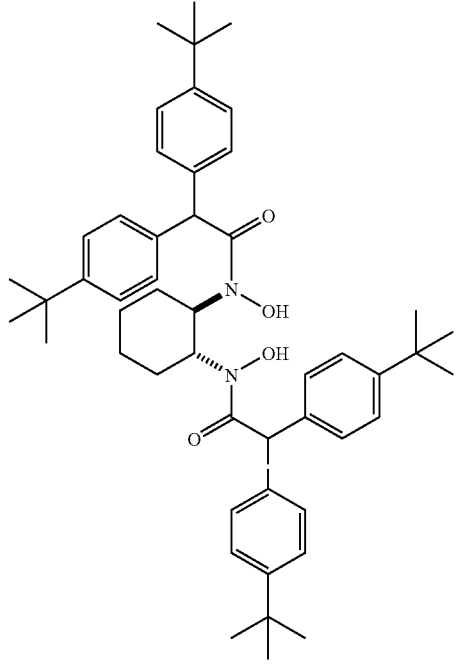

Id

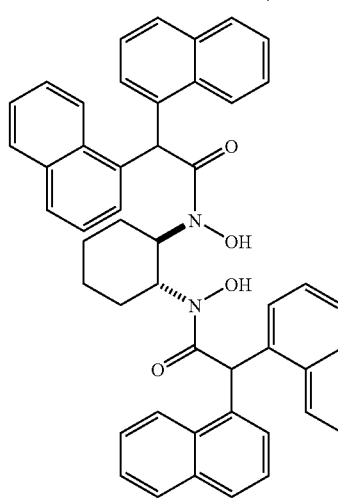

Ie

21
-continued
If
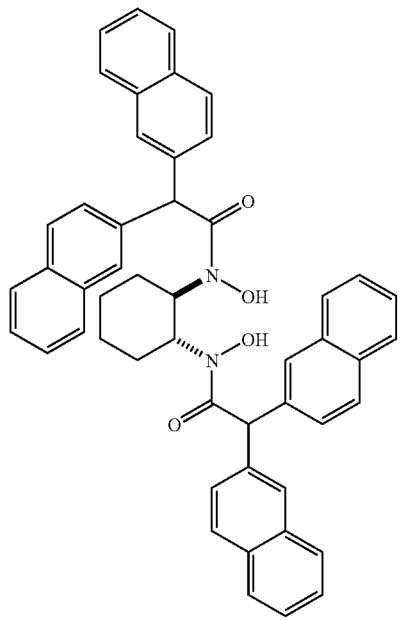
Ig
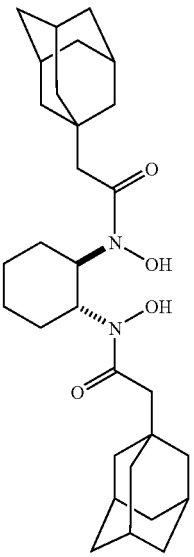
Ih
22
-continued
Ij
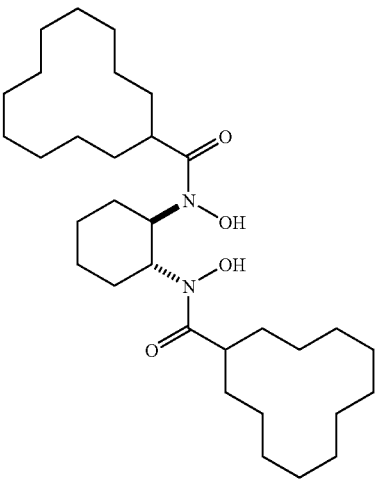
Ik
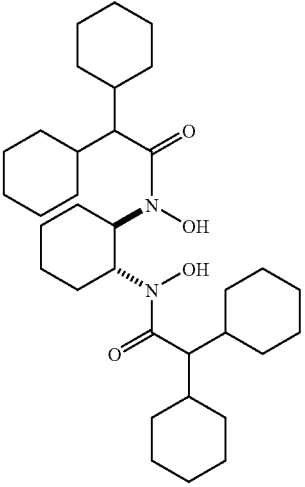
Il
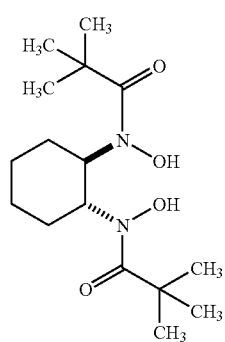

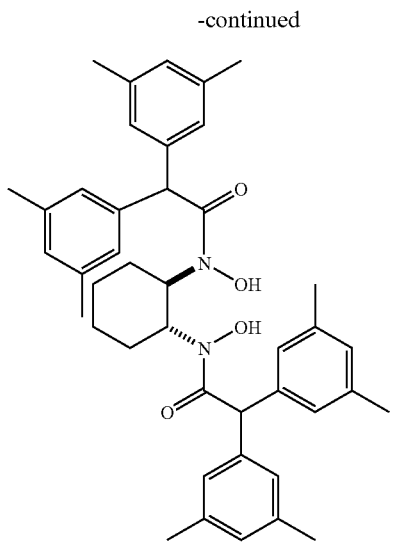

Im

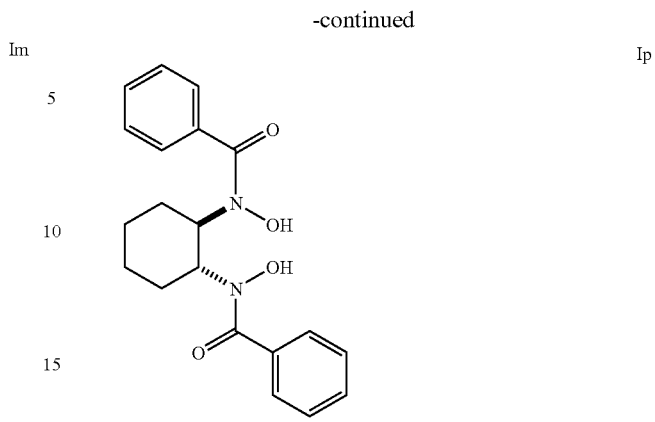

iN

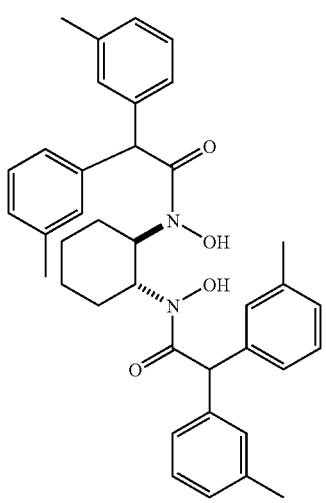

Io

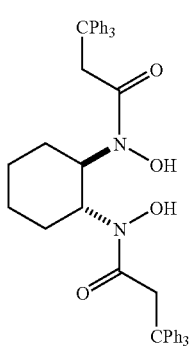

-continued

Ip

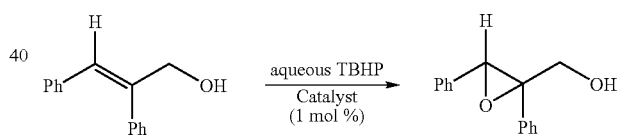

Table 1, demonstrates that the catalytic asymmetric oxidation, disclosed herein, can be performed with a variety of chiral bishydroxamic acid ligands. In fact, the results above reveal that this reaction will provide enantiomeric excesses with a wide range of chiral bishydroxamic acid ligands. This table also reveals that this reaction can be employed to epoxidize trans-2,3-diphenyl-2-propenol. It is important to note that one skilled in the art would realize that changing the identity and characteristics of the chiral bishydroxamic acid ligand will provide a means of optimizing both the enantiomeric excess and the yield of this reaction. Furthermore, Table 1 demonstrates that the reaction can be successfully carried out in both methylene chloride and toluene.

TABLE 1

Epoxidation of trans-2,3-diphenyl-2-propenol.

| Example | Ligand | Ligand/ VO(OPr$^i$)$_3$ | Solvent | Temp/time | % Yield | % ee- (config) |
|---|---|---|---|---|---|---|
| 1 | Ia | 2.0:1.0 | Toluene | 0° C., 15 h | 87 | 94 (RR) |
| 2 | Ib | 2.0:1.0 | Toluene | 0° C., 12 h | 77 | 91 (RR) |
| 3 | Ic | 2.0:1.0 | Toluene | 0° C., 12 h | 81 | 94 (RR) |
| 4 | Id | 2.0:1.0 | Toluene | 0° C., 12 h | 95 | 93 (RR) |
| 5 | Ie | 1.0:1.0 | Toluene | 0° C., 1 h | 23 | 92 (RR) |
| 6 | If | 2.0:1.0 | Toluene | 0° C., 11 h | 100 | 92 (RR) |
| 7 | Ig | 2.0:1.0 | Toluene | 0° C., 14.5 h | 74 | 86 (RR) |
| 8 | Ii | 1.5:1.0 | Toluene | 0° C., 12 h | 43 | 5 (RR) |
| 9 | Ij | 1.5:1.0 | Toluene | 0° C., 12 h | 79 | 96 (RR) |
| 10 | Ik | 2.0:1.0 | CH$_2$Cl$_2$ | 0° C., 20 h | 76 | 98 (RR) |
| 11 | Il | 2.0:1.0 | CH$_2$Cl$_2$ | 0° C., 20 h | 75 | 99 (RR) |
| 12[a] | Im | 2.0:1.0 | CH$_2$Cl$_2$ | 0° C., 9 h | 78 | 91 (RR) |
| 13[a] | In | 2.0:1.0 | CH$_2$Cl$_2$ | 0° C., 9 h | 84 | 94 (RR) |
| 14 | Io | 2.0:1.0 | Toluene | 0° C., 18 h | 88 | 90 (RR) |

[a]anhydrous TBHP solution in CH$_2$Cl$_2$ was used.

Table 2, demonstrates the amenability of this reaction to the epoxidation of a substrate containing multiple alkenes.

In fact, the reaction shows selectivity for the allylic alkene. Table 2, also shows that good yields and enantiomeric excesses can be obtained with a large variety of chiral bishydroxamic acid ligands.

TABLE 2

Epoxidation of Geraniol.

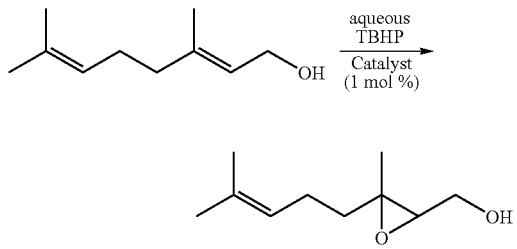

| Example | Ligand | Ligand/VO(OPr$^i$)$_3$ | Solvent | Temp/time | % Yield | % ee |
|---|---|---|---|---|---|---|
| 1 | Ia | 2.0:1.0 | Toluene | 0° C., 2 h | 50 | 76 |
| 2 | Ib | 2.0:1.0 | Toluene | 0° C., 24 h | 60 | 63 |
| 3 | Ic | 2.0:1.0 | Toluene | 0° C., 24 h | 71 | 67 |
| 4 | Id | 2.0:1.0 | Toluene | 0° C., 24 h | 44 | 56 |
| 5 | If | 2.0:1.0 | Toluene | 0° C., 5 h | 90 | 76 |
| 6 | Ig | 2.0:1.0 | Toluene | 0° C., 14 h | 66 | 72 |
| 7 | Ij | 1.5:1.0 | Toluene | 0° C., 19 h | 47 | 63 |
| 8 | Ik | 2.0:1.0 | CH$_2$Cl$_2$ | 0° C., 20 h | 70 | 74 |
| 9[a] | Il | 2.0:1.0 | CH$_2$Cl$_2$ | −10° C., 18 h | 60 | 84 |
| 10[a] | Im | 2.0:1.0 | CH$_2$Cl$_2$ | 0° C., 9 h | 67 | 83 |
| 11[a] | In | 2.0:1.0 | CH$_2$Cl$_2$ | 0° C., 3 h | 37 | 81 |
| 12 | Io | 2.0:1.0 | Toluene | 0° C., 18 h | 74 | 80 |
| 13[a] | Im | 2.0:1.0 | CH$_2$Cl$_2$ | −10° C., 7 h | 31 | 85 |
| 14[a] | In | 2.0 1.0 | CH$_2$Cl$_2$ | −10° C., 7 h | 38 | 84 |
| 15[a] | Im | 2.0 1.0 | CH$_2$Cl$_2$ | −20° C., 24 h | 42 | 89 |
| 16[a] | In | 2.0:1.0 | CH$_2$Cl$_2$ | −20° C., 24 h | 49 | 88 |
| 17 | Io | 2.0:1.0 | CH$_2$Cl$_2$ | 0° C., 18 h | 73 | 83 |

[a] anhydrous TBHP solution in CH$_2$Cl$_2$ was utilized.

Table 3 reveals that this catalytic asymmetric oxidation can be run under a variety of reaction conditions, including a broad range of temperatures. One skilled in the art will realize that changing conditions such as the vanadium source, the temperature, the oxidant, and the ligand to metal ratio will allow optimization of both the yield and the enantiomeric excess. Furthermore, the results provided above demonstrate that both CHP and TBHP can be employed as the hydroperoxide oxidant.

TABLE 3

The Effect of Variations in Reaction Conditions.

| Example | Vanadium | Vanadium:Ia | Oxidant | Temp/time | Yield | % ee (config) |
|---|---|---|---|---|---|---|
| 1 | VO(OPr$^i$)$_3$ | 1.0:1.0 | CHP | rt, 4 h | 93 | 84 (RR) |
| 2 | VO(OPr$^i$)$_3$ | 1.0:1.0 | TBHP | rt, 12 h | 94 | 88 (RR) |
| 3 | VO(OPr$^i$)$_3$ | 1.0:1.0 | TBHP | 0° C., 6 h | 84 | 94 (RR) |
| 4 | VO(OPr$^i$)$_3$ | 1.0:1.0 | TBHP | −20° C., 40 h | 84 | 97 (RR) |
| 5 | VO(OPr$^i$)$_3$ | 1.0:2.0 | TBHP | rt, 6 h | 96 | 92 (RR) |
| 6 | VO(OPr$^i$)$_3$ | 1.0:2 0 | TBHP | 0° C., 15 h | 87 | 95 (RR) |
| 7 | VO(OPr$^i$)$_3$ | 1.0:2.0 | TBHP | −20° C., 30 h | 89 | 96 (RR) |
| 8 | VO(OPr$^i$)$_3$ | 1.0:3.0 | TBHP | rt, 6 h | 96 | 92 (RR) |
| 9 | VO(OPr$^i$)$_3$ | 1.0:3.0 | TBHP | 0° C., 15 h | 86 | 94 (RR) |
| 10 | VO(acac)$_2$ | 1.0:1.0 | TBHP | rt, 6 h | 96 | 90 (RR) |
| 11 | VO(acac)$_2$ | 1.0:1.0 | TBHP | 0° C., 12 h | 93 | 94 (RR) |
| 12 | VO(acac)$_2$ | 1.0:1.0 | TBHP | −20° C., 40 h | 81 | 97 (RR) |
| 13 | VO(acac)$_2$ | 1.0:2.0 | TBHP | rt, 6 h | 96 | 92 (RR) |
| 14 | VO(acac)$_2$ | 1.0:2.0 | TBHP | 0° C., 12 h | 90 | 95 (RR) |
| 15 | VO(acac)$_2$ | 1.0:2.0 | TBHP | −20° C., 30 h | 85 | 96 (RR) |
| 16 | VO(acac)$_2$ | 1.0:3.0 | TBHP | 0° C., 6 h | 95 | 90 (RR) |
| 17 | VO(acac)$_2$ | 1.0:3.0 | TBHP | rt, 12 h | 84 | 93 (RR) |

Table 4 shows that the reaction can be performed under a variety of reaction conditions. These results also reveal that the reaction can be carried out under aqueous conditions, since aqueous hydroperoxide provided both good yields and enantiomeric excesses.

TABLE 4

Epoxidation of Geraniol: The Effect of Variations of the Oxidant, the Solvent, and the Vanadium Source.

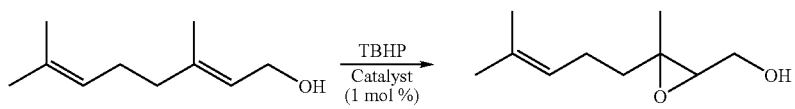

Complexation of the Ligand and Vanadium

| Entry | Ligand | Vanadium | Ligand to Vanadium | Solvent Temp/time | Oxidant | Temp/time | Yield | % ee |
|---|---|---|---|---|---|---|---|---|
| 1 | Ia | VO(OPr$^i$)$_3$ | 1.5:1.0 | Toluene, rt, 1 h | Trityl hydroperoxide | 0° C., 68 h | 40% | 15 |
| 2 | Ia | VO(OEt)$_3$ | 1.5:1.0 | Toluene, rt, 1 h | Aqueous TBHP | 0° C., 19 h | 41% | 68 |
| 3 | Ia | VO(OPr$^i$)$_3$ | 1.5:1.0 | Toluene, rt, 1 h | Aqueous TBHP | 0° C., 19 h | 80% | 72 |
| 4[a,b] | Ia | VO(OPr$^i$)$_3$ | 1.5:1.0 | CH$_2$Cl$_2$,[a] rt 1 h | Anhydrous TBHP | 0° C., 19 h | 85% | 78 |

TABLE 4-continued

Epoxidation of Geraniol: The Effect of Variations of the Oxidant, the Solvent, and the Vanadium Source.

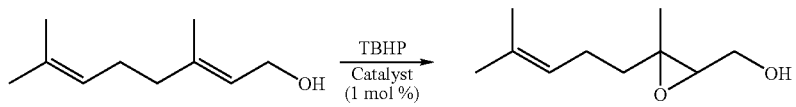

Complexation of the Ligand and Vanadium

| Entry | Ligand | Vandium | Ligand to Vanadium | Solvent Temp/time | Oxidant | Oxidation Conditions Temp/time | Yield | % ee |
|---|---|---|---|---|---|---|---|---|
| 5 | Il | VO(OPr$^i$)$_3$ | 2.0:1.0 | Toluene, rt, 1 h | Aqueous TBHP | −10° C., 18 h | 65% | 76 |
| 6 | Il | VO(OPr$^i$)$_3$ | 2.0:1.0 | CH$_2$Cl$_2$, rt, 1 h | Anhydrous TBHP | −10° C., 18 h | 60% | 84 |

[a]Oxidation was performed under an atmosphere of nitrogen. Anhydrous TBHP in CH$_2$Cl$_2$ was utilized for the oxidation.
[b]solution of the ligand in CH2Cl2 was heated heated with hot gun prior to addition of the vanadium isopropoxide and then stirred at room temperature for 1 h Table 5 explores how different oxidants, solvents and vanadium sources influence the yield and the enantiomeric excess of this asymmetric oxidation. The results in Table 5 show that the reaction can be successfully carried out with not only VO(Opr$^i$)$_3$ and VO(acac)$_3$, but also with VO(OEt)$_3$. This data also reveals that the reaction is compatible with toluene, methylene chloride, and ethyl acetate.

TABLE 5

Epoxidation of Geraniol: The Effect of Variations of the Oxidant, the Solvent, and the Vanadium Source.

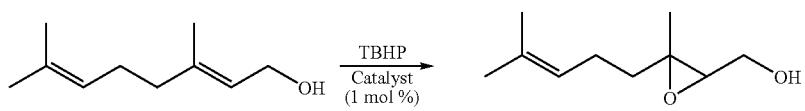

Complexation of the Ligand and Vanadium

| Entry | Ligand | Vanadium | Ligand/ Vanadium | Solvent | Temp/time | Oxidant | Oxidation Conditions Temp/time | Yield | % ee[b] |
|---|---|---|---|---|---|---|---|---|---|
| 1 | Io | VO(OPr$^i$)$_3$ | 2.0:1.0 | Toluene | rt, 1 h | Aqueous TBHP | 0° C., 18 h | 74% | 81 |
| 2 | Io | VO(OPr$^i$)$_3$ | 2.0:1.0 | CH$_2$Cl$_2$ | rt, 1 h | Aqueous TBHP | 0° C., 18 h | 73% | 83 |
| 3 | Io | VO(OPr$^i$)$_3$ | 2.0:1.0 | CHCl$_3$ | rt, 1 h | Aqueous TBHP | 0° C., 18 h | 71% | 77 |
| 4 | Io | VO(OPr$^i$)$_3$ | 2.0:1.0 | EtOAc | rt, 1 h | Aqueous TBHP | 0° C., 18 h | 34% | 76 |
| 5 | Io | VO(OPr$^i$)$_3$ | 2.0:1.0 | DMF | rt, 1 h | Aqueous TBHP | 0° C., 18 h | —[a] | — |
| 6 | Io | VO(OPr$^i$)$_3$ | 2.0:1.0 | Toluene | rt, 1 h | Anhydrous TBHP | 0° C., 18 h | 70% | 81 |
| 7 | Io | VO(OPr$^i$)$_3$ | 2.0:1.0 | CH$_2$Cl$_2$ | rt, 1 h | Anhydrous TBHP | 0° C., 18 h | 30% | 79 |
| 8 | Io | VO(OEt)$_3$ | 2.0:1.0 | CH$_2$Cl$_2$ | rt, 1 h | Aqueous TBHP | 0° C., 18 h | 90% | 83 |
| 9 | Io | VO(acac)$_2$ | 2.0:1.0 | CH$_2$Cl$_2$ | rt, 1 h | Aqueous TBHP | 0° C., 18 h | 80% | 83 |
| 10 | Io | VO(OPr$^i$)$_3$ | 2.0:1.0 | Toluene | rt, 1 h | Aqueous TBHP | −20° C., 43 h | 57% | 80 |
| 11 | Io | VO(OPr$^i$)$_3$ | 2.0:1.0 | CH$_2$Cl$_2$ | rt, 1 h | Aqueous TBHP | −20° C., 43 h | 38% | 80 |
| 12 | Io | VO(acac)$_2$ | 2.0:1.0 | Toluene | rt, 1 h | Aqueous TBHP | −20° C., 69 h | 54% | 79 |
| 13 | Io | VO(acac)$_2$ | 2.0:1.0 | CH$_2$Cl$_2$ | rt, 1 h | Aqueous TBHP | −20° C., 69 h | 60% | 78 |

[a]No product was observed in TLC

Table 6 reveals that several different chiral bishydroxamic acid ligands can be utilitzed to epoxidize cinnamyl alcohol. In each case high enantioselectivies were achieved with respect to the desired epoxidation product.

TABLE 6

Epoxidation of trans disubstituted allylic alcohols.

R⌒⌒OH + Catalyst (2 mol %), Aqueous TBHP, Solvent → R-epoxide-OH

| | | Complexation of the Ligand and Vanadium | | | | Oxidation Conditions | | | |
|---|---|---|---|---|---|---|---|---|---|
| Example | Product | Ligand | Vanadium | Solvent | Temp/time | Oxidant | Temp/time | % Yield | % ee |
| 1 | $C_5H_{11}$-epoxide-OH | Ia | $VO(acac)_2$ | $CH_2Cl_2$ | rt, 1 h | Aqueous TBHP | 0° C., 45 h | 50[a] | 93 |
| 2 | | Io | $VO(acac)_2$ | $CH_2Cl_2$ | rt, 1 h | Aqueous TBHP | 0° C., 45 h | 59[a] | 77 |
| 3 | $C_5H_{11}$-epoxide-OH | Ia | $VO(acac)_2$ | $CH_2Cl_2$ | rt, 1 h | Aqueous TBHP | 0° C., 49 h | 40% | 92 |
| 4 | | Io | $VO(acac)_2$ | $CH_2Cl_2$ | rt, 1 h | Aqueous TBHP | 0° C., 49 h | 55% | 78 |
| 5 | Ph-epoxide-OH | Ia[b] | $VO(acac)_2$ | Toluene | rt, 1 h | Aqueous TBHP | 0° C., 43 h | 45%[a] | 95 |
| 6 | | Ia | $VO(acac)_2$ | Toluene $CH_2Cl_2$ | rt, 1 h | Aqueous TBHP | 0° C., 69 h | 33% | 93 |
| 7 | | Ia | $VO(acac)_2$ | | rt, 1 h | Aqueous TBHP | 0° C., 69 h | 40% | 94 |
| 8 | | Ik[b] | $VO(OPr^i)_3$ | Toluene | rt, 1 h | Aqueous TBHP | 0° C., 43 h | 49%[a] | 83 |
| 9 | | Io[b] | $VO(acac)_2$ | Toluene | rt, 1 h | Aqueous TBHP | 0° C., 48 h | 40%[a] | 84 |

[a]determined by 1H NMR analysis of the unpurified product.
[b]Catalyst 1 mol %

Table 7 explores the ability of this asymmetric oxidation to epoxidize nerol and (E)-3-phenylbut-2-en-1-ol. In this case, enantiomeric excesses, in conjunction with high yields, were obtained with regard to the epoxidation of the allylic alkene. Furthermore, these successful results were obtained with a number of different chiral bishydroxamic acid ligands.

TABLE 7

Epoxidation of Nerol and (E)-3-phenylbut-2-en-1-ol.

| | | Complexation of the Ligand and Vanadium | | | | Oxidation Conditions | | | |
|---|---|---|---|---|---|---|---|---|---|
| Entry | Product | Ligand | Vanadium | Solvent | Temp/time | Oxidant | Temp/time | % Yield | % ee |
| 1 | Ph-epoxide-OH | Ia | $VO(acac)_2$ | Toluene | rt, 1 h | Aqueous TBHP | 0° C., 20.5 h | 8[a] | 84 |
| 2 | | Io | $VO(acac)_2$ | Toluene | rt, 1 h | Aqueous T8HP | 0° C., 20.5 h | 23[a] | 88 |
| 3 | | Ia | $VO(OPr^i)_3$ | $CH_2Cl_2$ | rt, 1 h | Aqueous TBHP | 0° C., 22 h | 36 | 85 |
| 4 | | Io | $VO(OPr^i)_3$ | $CH_2Cl_2$ | rt, 1 h | Aqueous TBHP | 0° C., 22 h | 81 | 92 |
| 5 | | Il | $VO(OPr^i)_3$ | $CH_2Cl_2$ | rt, 1 h | Aqueous TBHP | 0° C., 18 h | 83 | 88 |
| 6 | | Ia | $VO(acac)_2$ | Toluene | rt, 1 h | Aqueous TBHP | 0° C., 20.5 h | 83 | 70 |
| 7 | | Io | $VO(acac)_2$ | Toluene | rt, 1 h | Aqueous TBHP | 0° C., 20.5 h | 82 | 88 |
| 8 | | In | $VO(OPr^i)_3$ | $CH_2Cl_2$ | rt, 1 h | Anhydrous TBHP | 0° C., 18 h | 92 | 85 |
| 9 | | If | $VO(OPr^i)_3$ | $CH_2Cl_2$ | rt, 1 h | Anhydrous TBHP | 0° C., 10 h | 96 | 80 |

Table 8 provides results for the epoxidation of α-methylcinnamyl In this case, both high yields and enantiomeric excesses were with a number of different chiral bishydroxamic acid ligands.

TABLE 8

Epoxidation of α-Methylcinnamyl Alcohol.

| Entry | Ligand | Vanadium Source | Catalyst loading | Oxidant | Solvent Temp/time | Isolated Yield | % ee |
|---|---|---|---|---|---|---|---|
| 1 | Ia | VO(acac)$_2$ | 1 mol % | Aqueous TBHP | Toluene, 0° C., 44 h | 76% | 95 |
| 2 | Io | VO(acac)$_2$ | 1 mol % | Aqueous TBHP | Toluene, 0° C., 44 h | 86% | 87 |
| 3 | In | VO(OPr$^i$)$_3$ | 1 mol % | Anhydrous TBHP | CH$_2$Cl$_2$ 0° C., 18 h | 92% | 93 |
| 4 | If | VO(OPr$^i$)$_3$ | 1 mol % | Anhydrous TBHP | CH$_2$Cl$_2$ 0° C., 10 h | 96% | 90 |
| 5 | Il | VO(OPr$^i$)$_3$ | 1 mol % | Aqueous TBHP | CH$_2$Cl$_2$ 0° C., 17 h | 88% | 95 |

Table 9 demonstrates that this reaction can be successfully applied to cyclic alkene substrates, in this case cyclohex-1-enyl-methanol. In fact, high enantiomeric excess were obtained, in good yields, with three different chiral bishydroxamic acid ligands.

TABLE 9

Epoxidation of Cyclohex-1-enyl-methanol.

| | | | Complexation of the Ligand and Vanadium | | | | | |
|---|---|---|---|---|---|---|---|---|
| | | | Ligand/ | | | Oxidation Conditions | | |
| Entry | Ligand | Vanadium | Vanadium | Solvent | Temp/time | Oxidant | Temp/time | Yield | % ee |
| 1 | Ia | VO(acac)$_2$ | 2.0:1.0 | Toluene | rt, 1 h | Aqueous TBHP | 0° C., 21.5 h | 66 | 93 |
| 2 | Io | VO(acac)$_2$ | 2.0:1.0 | Toluene | rt, 1 h | Aqueous TBHP | 0° C., 21.5 h | 76 | 73 |
| 3 | Il | VO(OPr$^i$)$_2$ | 2.0:1.0 | CH$_2$Cl$_2$ | rt, 1 h | Aqueous TBHP | 0° C., 17 h | 59 | 88 |
| 4 | If | VO(OPr$^i$)$_3$ | 2.0:1.0 | CH$_2$Cl$_2$ | rt, 1 h | Anhydrous TBHP | 0° C., 12 h | 94% | 92 |

Table 10 reveals that the reaction disclosed herein can also successfully epoxidize a five membered cyclic alkene.

TABLE 10

Epoxidation of Cyclopent-1-enyl-methanol.

| | | | Complexation of the Ligand and Vanadium | | | | | |
|---|---|---|---|---|---|---|---|---|
| | | | Ligand/ | | | Oxidation Conditions | | |
| Entry | Ligand | Vanadium | Vanadium | Solvent | Temp/time | Oxidant | Temp/time | Yield | % ee |
| 1 | Ia | VO(acac)$_2$ | 2.0:1.0 | Toluene | rt, 1 h | Aqueous TBHP | 0° C., 20.5 h | 52% | 90 |
| 2 | Io | VO(acac)$_2$ | 2.0:1.0 | Toluene | rt, 1 h | Aqueous TBHP | 0° C., 20.5 h | 72% | 75 |

TABLE 10-continued

Epoxidation of Cyclopent-1-enyl-methanol.

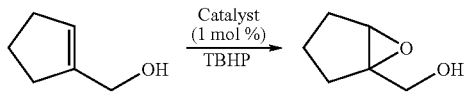

Complexation of the Ligand and Vanadium

| | | Ligand/ | | | | Oxidation Conditions | | | |
|---|---|---|---|---|---|---|---|---|---|
| Entry | Ligand | Vanadium | Vanadium | Solvent | Temp/time | Oxidant | Temp/time | Yield | % ee |
| 3 | If | VO(OPr$^i$)$_3$ | 2.0:1.0 | CH$_2$Cl$_2$ | rt, 1 h | Anhydrous TBHP | 0° C., 10 h | 94% | 69 |
| 4 | Im | VO(OPr$^i$)$_3$ | 2.0:1.0 | CH$_2$Cl$_2$ | rt, 1 h | Anhydrous TBHP | 0° C., 18 h | 95% | 78 |

Table 11 demonstrates that a cis-alkene can be utilized as the epoxidation substrate. The data shows that the yield may vary with changes in the nature of the bishyroxamic acid ligand. However, it appears that drastic changes in the character of the chiral bishydroxamic acid ligand may have only a minimal influence with respect to the enantiomeric excess.

TABLE 11

Epoxidation of (Z)-Hex-2-en-ol.

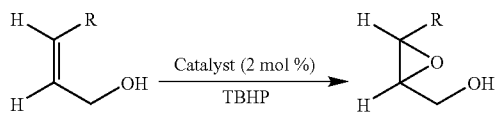

| Entry | | Ligand | Vanadium | Solvent | Temp/time | Oxidant | Temp/time | % Yield | % ee |
|---|---|---|---|---|---|---|---|---|---|
| 1 | Ph | Ia | VO(acac)$_2$ | CH$_2$Cl$_2$ | rt, 1 h | Aqueous TBHP | 0° C., 5 days | 11 | 74 |
| 2 | | Io | VO(acac)$_2$ | CH$_2$Cl$_2$ | rt, 1 h | Aqueous TBHP | 0° C., 5 days | 55 | 91 |
| 3 | | Io | VO(acac)$_2$ | CH$_2$Cl$_2$ | rt, 1 h | Aqueous TBHP | RT, 26 h | 68 | 89 |
| 4 | | Il | VO(OPr$^i$)3 | CH$_2$Cl$_2$ | rt, 1 h | Aqueous TBHP | 0° C., 5 days | 49 | 87 |
| 5 | C$_3$H$_7$ | Ia | VO(acac)$_2$ | CH$_2$Cl$_2$ | rt, 1 h | Aqueous TBHP | 0° C., 92 h | 28 | 80 |
| 6 | | Il | VO(OPr$^i$)$_2$ | CH$_2$Cl$_2$ | rt, 1 h | Aqueous TBHP | 0° C., 92 h | 50 | 87 |
| 7 | | Io | VO(acac)$_2$ | CH$_2$Cl$_2$ | rt, 1 h | Aqueous TBHP | RT, 21 h | 89 | 91 |
| 8 | | Io | VO(acac)$_2$ | CH$_2$Cl$_2$ | rt, 1 h | Aqueous TBHP | 0° C., 46 h | 64 | 93 |
| 9 | C$_6$H$_{13}$ | Io | VO(acac)$_2$ | CH$_2$Cl$_2$ | rt, 1 h | Aqueous TBHP | 0° C., 46 h | 60% | 95 |

Table 12 demonstrates that the epoxidation of trans-2,3-diphenyl-2-propenol and geraniol can be successfully carried out using molybdenum as the metal, in this case $MoO(acac)_2$.

TABLE 12

Molybdenum Catalyzed Epoxidation.

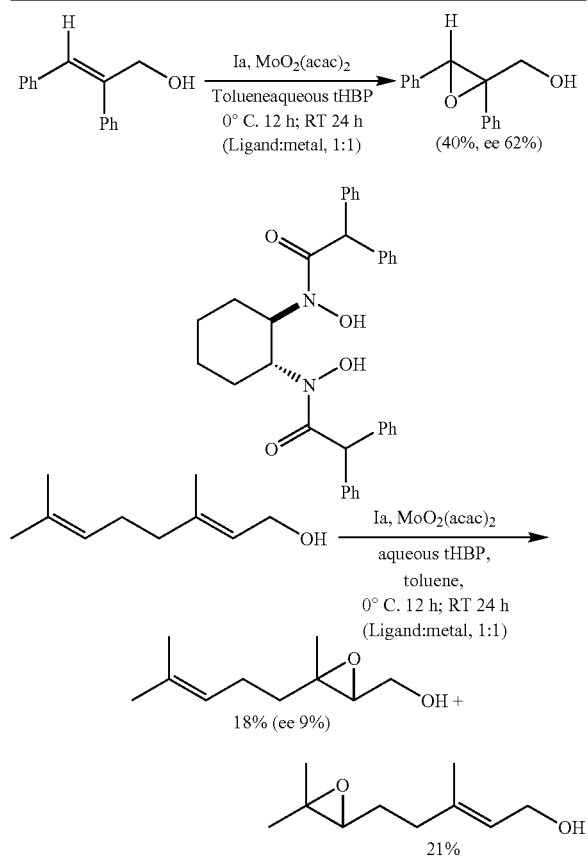

Table 13 shows that this reaction is also capable of successfully epoxidizing homoallylic alcohols.

TABLE 13

Epoxidation of Homoallylic Alcohol.

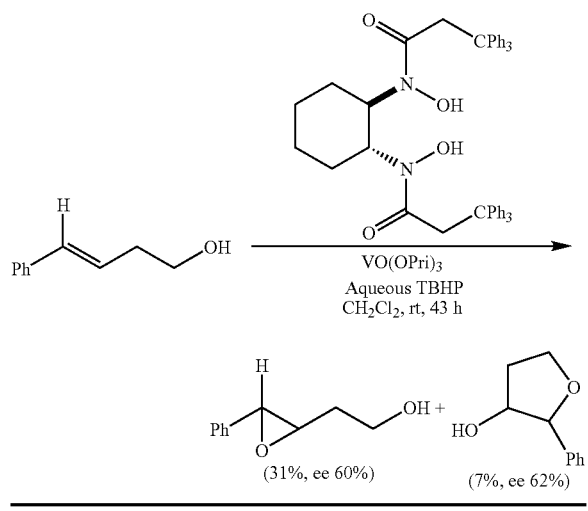

SYNTHETIC AND SPECTROSCOPIC EXAMPLES

Example 1

The preparation (R,R)-N,N'-Bis-(4-methoxybenzylidene)-cyclohexane-1,2-diamine (IVa) is shown below.

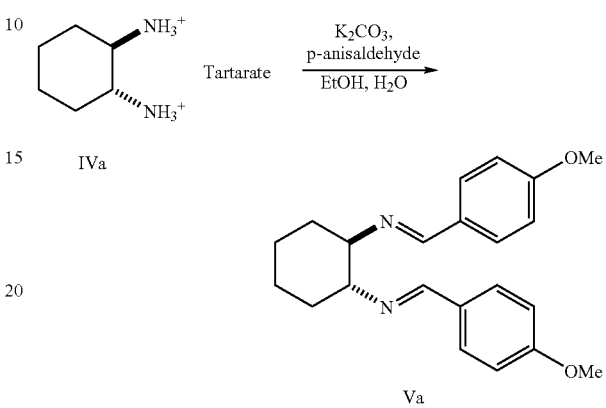

In this preparation, a mixture of diammonium salt (IVa) (21.2 g, 80.1 mmol), $K_2CO_3$ (22.1 g, 160 mmol), and de-ionized water (107 mL) was stirred until dissolution was achieved, and then ethanol (429 mL) was added. The resulting cloudy mixture was heated at 80° C., and a solution of p-anisaldehyde (21.8 g, 160 mmol) in ethanol (36 mL) was added in a steady stream over 30 min. The yellow slurry was stirred at the same temperature for 5 h before heating was discontinued. The reaction mixture was cooled to room temperature, and the water phase was separated and discarded. The organic phase was concentrated and toluene was added to the residue. It was then concentrated to remove any traces of water. The resulting residue was dissolved in chloroform, dried ($Na_2SO_4$) and filtered. The filtrate was evaporated to give crude Va as light yellow solid, which was purified by recrystalization from chloroform and hexanes: $R_f$ 0.6 (EtOAc/hexanes, 3:7); FTIR (film) $\upsilon_{max}$ 2929, 2855, 1643, 1606, 1579, 1512, 1463, 1303, 1250, 1165, 1032, 831 $cm^{-1}$; $^1H$ NMR (500 MHz, $CDCl_3$) δ8.13 (s, 2H), 7.52 (d, J=8.5 Hz, 4H), 6.83 (d, J=8.5 Hz, 4H), 3.79 (s, 6H), 3.37–3.32 (m, 2H), 1.87–1.77 (m, 6H), 1.49–1.46 (m, 2H); $^{13}C$ NMR (125 MHz, $CDCl_3$) δ 161.5 (C), 160.5 (CH), 129.7 (CH), 114.0 (CH), 74.0 ($CH_3$), 55.5 (CH), 33.3 ($CH_2$), 24.8 ($CH_2$). HRMS-ESI calcd for $C_{22}H_{27}O_6N_2$ $[M+H]^+$ 351.2073, found 351.2076.

Example 2

The preparation of Dioxaziridine Via is shown below.

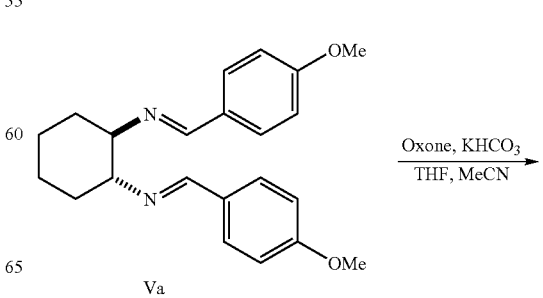

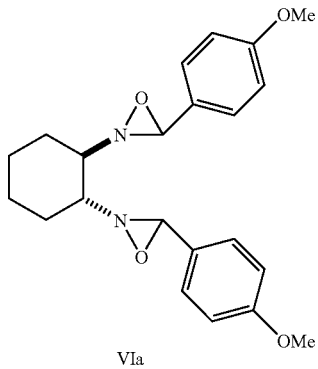

VIa

To a stirred solution of diimine Va (10.5 g, 30.0 mmol) in MeCN (180 mL) and THF (360 mL), at room temperature, was added an aqueous solution (300 mL) of $KHCO_3$ (50.5 g, 504 mmol) followed by an aqueous solution (300 mL) of oxone (44 g, 72 mmol). After stirring for 2 h 15 min, the reaction mixture was diluted with $CH_2Cl_2$ (600 mL). The biphasic mixture was separated and the aqueous portion was extracted with $CH_2Cl_2$ (2×300 mL) and the combined organic extracts dried ($Na_2SO_4$) and filtered. The filtrate was concentrated under reduced pressure to provide crude dioxaziridine VIa (11.1 g) which was used in the following step without further purification: Major diastereomer FTIR (film) $\upsilon_{max}$ 2935, 1615, 1517, 1309, 1456, 1437, 1310, 1252, 1171, 1031, 821, cm$^{-1}$; $^1$H NMR (500 MHz, CDCl$_3$) δ 7.02–6.79 (m, 4H), 6.59–7.6.56 (m, 4H), 4.39 (s, 2H), 3.81 (s, 6H), 2.39–2.37 (m, 2H, CHH'), 2.22–2.20 (m, 2H), 1.83–1.81 (m, 2H), 1.58–1.51 (m, 2H), 1.31–1.27 (m, 2H); $^{13}$C NMR (125 MHz, CDCl$_3$) δ 160.7 (C), 129.0 (CH), 126.5 (C), 113.8 (CH), 81.6 (CH), 72.4 (CH$_3$/CH), 55.4 (CH$_3$/CH), 30.3 (CH$_2$), 24.1 (CH$_2$). HRMS-ESI calcd. for $C_{22}H_{26}O_4N_2Na$ [M+Na]$^+$ 405.1788, found 405.1790.

Example 3

The preparation of Bis-hydroxylamine dihydrochloride VIIa is shown below.

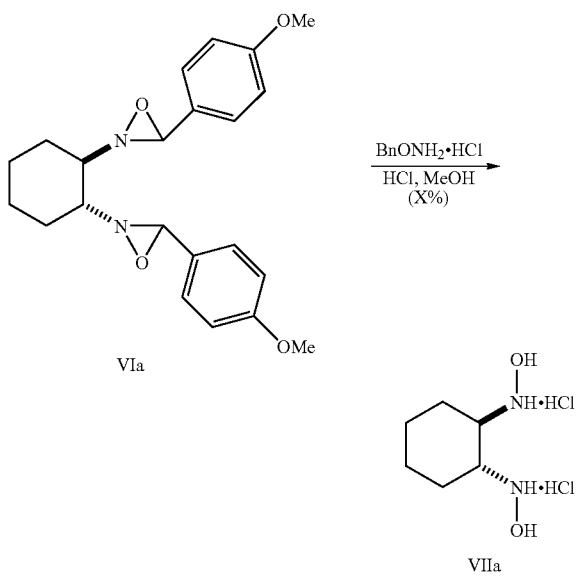

To a mixture of the unpurified product VIa (11.1 g) obtained from the previous oxidation reaction and benzyloxyhydroxylamine hydrochloride (BnONH$_2$.HCl) (8.8 g, 55.1 mmol) was treated with anhydrous methanol (immediately) followed by 1 M HCl in MeOH (94 mL, 94 mmol). The resulting mixture was stirred for 20 minutes. The reaction mixture was then concentrated under reduced pressure to dryness. Et$_2$O (200 mL) and de-ionized water (100 mL) was added. The bi-layer was separated and the organic part was extracted with de-ionized water (20 mL). Combined aqueous portion was washed with Et$_2$O (2×100 mL). The aqueous portion was concentrated to 60–75 mL and resulting white solid (BnONH$_2$.HCl) was filtered off and the filtrate was concentrated under reduced pressure to provide bis-hydroxylamine dihydrochloride VIIa (6.95 g) as an oily solid which contained 5–10% of BnONH$_2$.HCl This material was utilized in the next step without any purification: $^1$H NMR (400 MHz, D$_2$O) δ 3.66–3.62 (m, 2H), 2.02–1.98 (m, 2H), 1.69–1.66 (m, 2H), 1.41–1.37 (m, 4H), 1.20–1.15 (m, 2H; $^{13}$C NMR (100 MHz, D$_2$O) δ 58.6 (CH), 25.1 (CH$_2$), 22.1 (CH$_2$).

Example 4

Two methods for the preparation of (R,R)-O,O'-bistrimethylsilyl cyclohexyl-1,2-dihydroxylamine (VIIIa) are shown below as Method A and Method B.

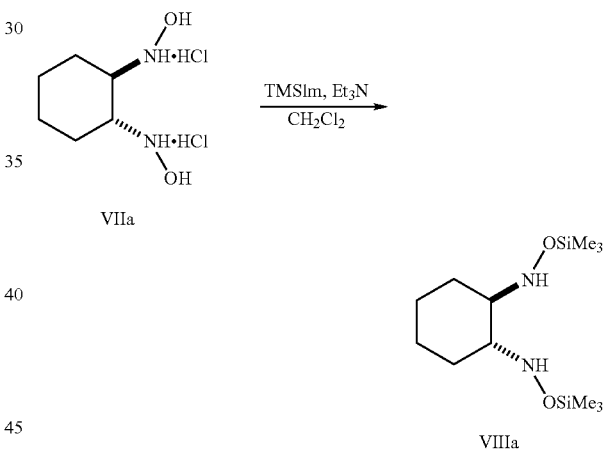

Method A: To a suspension of dihydroxylamine dihydrochloride VIIa (5.52 g, 25.2 mmol) in pentane (30 mL) at room temperature was added triethylamine (8.5 mL, 60.6 mmol) under nitrogen atmosphere. After stirring for 12 h at room temperature, the mixture was treated drop wise with 1-(trimethylsilyl)imidazole (TMSIm) (7.7 mL, 50.5 mmol) and stirred for another 9 h. The resulting suspension was filtrated through pad of Celite and the filtrate was concentrated under reduced pressure to give 0,0'-bistrimethylsilyl-cyclohexyl-1,2-dihydroxylamine (VIIIa) as yellow oil (5.85 g, 80% yield), which was used in the following reaction without further purification. $^1$H NMR (400 MHz, CDCl$_3$) δ 5.60 (br s, 2H), 2.68–2.65 (m, 2H), 2.19–2.15 (m, 2H), 1.23–1.13 (m, 4H), 0.14 (s, 18H).

Method B: To a stirred suspension of VIIa (382 mg, 1.74 mmol) and pyridine (1 mL) in CH$_2$Cl$_2$ (4 mL) at room temperature was added Et$_3$N (384 μL, 2.75 mmol). After 15 min, trimethylsilyl imidazole (620 μL, 4.2 mmol) was added and stirring was continued for 16 h. The reaction mixture was then diluted pentane (15 mL) and filtered through a pad of celite. The filtrate was concentrated under reduced pressure to provide VIIIa (432 mg, 86%) which was used in the coupling reaction without further purification. $^1$H NMR (400 MHz, CDCl$_3$) δ 5.60 (br s, 2H), 2.68–2.65 (m, 2H), 2.19–2.15 (m, 2H), 1.23–1.13 (m, 4H), 0.14 (s, 18H).

Example 5

Three methods for the preparation of (R,R)-O,O'-bistriethylsilylcyclohexyl-1,2-dihydroxylamine (XIIIb) are shown below and are designated Method A, Method B, and Method C. When referring triethylsilyl chloride, it can be abbreviated as TESCl.

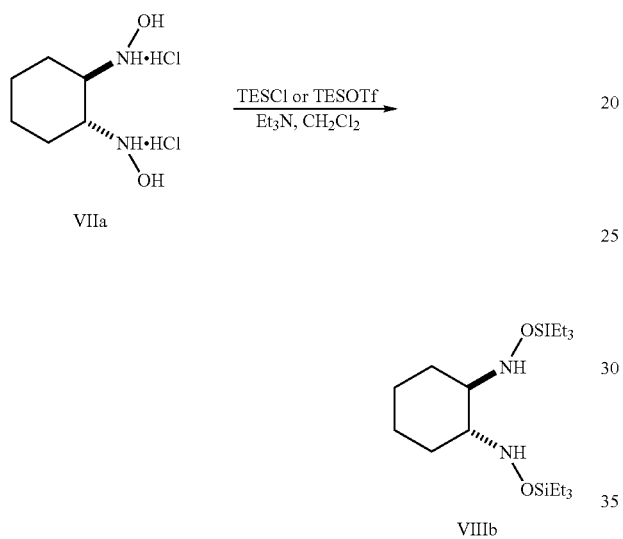

Method A: To a suspension of VIIIa (6.95 g) in CH$_2$Cl$_2$ (70 mL) at room was added Et$_3$N (12.6 mL, 90 mmol). After stirring 30 min, the reaction mixture was cooled to −30° C., and 2,6-lutidine (17.4 mL, 150 mmol) then triethylsilyl trifluoromethanesulfonate (TESOTf) (34 mL, 150 mmol). After 2 min, the CO$_2$/acetone cooling bath was removed and the reaction mixture stirred for 6 h at room temperature, then poured into brine (10 mL) and extracted with CH$_2$Cl$_2$ (2×200 mL). The combined organic extracts were dried (Na$_2$SO$_4$), filtered, and concentrated under reduced pressure. The residue was purified by flash chromatography over silica gel (EtOAc/hexanes, 1:99) to provide VIIIb (5.60 g, 50%) as a colorless oil: R$_f$ 0.6 (EtOAc/hexanes, 1:9); FTIR (film) υ$_{max}$ 2954, 2876, 1557, 1540, 1458, 1417, 1238, 1072, 1008, 883, 841, 738 cm$^{-1}$; $^1$H NMR (400 MHz, CDCl$_3$) δ 5.46 (br s, 2H), 2.66–2.63 (m, 2H), 2.19–2.18 (m, 2H), 1.71–170 (m, 2H), 0.98 (t, J=8.0 Hz, 18H), 0.67 (q, J=8.0 Hz, 12H); $^{13}$C NMR (125 MHz, CDCl$_3$) δ 63.1 (CH), 30.6 (CH$_2$), 24.8 (CH$_2$), 7.11 (CH$_3$), 4.3 (CH$_2$). HRMS-ESI calcd for C$_{18}$H$_{42}$O$_2$N$_2$Si$_2$Na [M+Na]$^+$ 397.2683, found 397.2690.

Method B: To a stirred suspension of VIIa (170 mg, 0.77 mmol) and pyridine (2 mL) in CH$_2$Cl$_2$ (1 mL) at room temperature was added Et$_3$N (215 μL, 0.15 mmol). After 30 min, triethylsilyl chloride (TMSCl) (775 μL, 4.62 mmol) was added and stirring was continued for 48 h, then poured into brine and extracted with CH$_2$Cl$_2$ (2×20 mL) The combined organic extracts were dried (Na$_2$SO$_4$), filtered, and concentrated under reduced pressure. The residue was purified by flash column chromatography over silica gel (EtOAc/hexanes, 0.5:99.5) to provide VIIIb (156 mg, 54%) as a colorless oil: R$_f$ 0.6 (EtOAc/hexanes, 1:9); FTIR (film) υ$_{max}$ 2954, 2876, 1557, 1540, 1458, 1417, 1238, 1072, 1008, 883, 841, 738 cm$^{-1}$; $^1$H NMR (400 MHz, CDCl$_3$) δ 5.46 (br s, 2H), 2.66–2.63 (m, 2H), 2.19–2.18 (m, 2H), 1.71–170 (m, 2H), 0.98 (t, J=8.0 Hz, 18H), 0.67 (q, J=8.0 Hz, 12H). $^{13}$C NMR (125 MHz, CDCl$_3$) δ 63.1 (CH), 30.6 (CH$_2$), 24.8 (CH$_2$), 7.11 (CH$_3$), 4.3 (CH$_2$).

Method C: To a stirred suspension of VIIa (2.24 g, 10.2 mmol) in CH$_2$Cl$_2$ (40 mL) at room temperature was added Et$_3$N (3.70 mL, 25.6 mmol). After 1 h (to the resulting cloudy white suspension) dimethyl aminopyridine (DMAP) (374 mg, 3.06 mmol), imidazole (4.17 g, 61.4 mmol) followed by triethylsilyl chloride (6.90 mL, 40.9 mmol) were added and stirring was continued 16 h, then poured into an aqueous solution of NaHCO$_3$ (5.16 g, 61.4 mmol) and extracted with EtOAc (2×100 mL). The combined organic extracts were dried (Na$_2$SO$_4$), filtered, and concentrated under reduced pressure. The residue was purified by flash column chromatography over silica gel (EtOAc/hexanes, 0.5:99.5) to provide VIIIb (4.23 g) which contained diethylsilyl ether as 1:1 mixture. This compound was kept under reduced pressure to remove diethylsilyl ether: R$_f$ 0.6 (EtOAc/hexanes, 1:9); FTIR (film) υ$_{max}$ 2954, 2876, 1557, 1540, 1458, 1417, 1238, 1072, 1008, 883, 841, 738 cm$^{-1}$; $^1$H NMR (400 MHz, CDCl$_3$) δ 5.46 (br s, 2H), 2.66–2.63 (m, 2H), 2.19–2.18 (m, 2H), 1.71–170 (m, 2H), 0.98 (t, J=8.0 Hz, 18H), 0.67 (q, J=8.0 Hz, 12H). $^{13}$C NMR (125 MHz, CDCl$_3$) δ 63.1 (CH), 30.6 (CH$_2$), 24.8 (CH$_2$), 7.11 (CH$_3$), 4.3 (CH$_2$).

Example 6

Three general procedures for condensation of the silyl protected dihydroxylamine with an acid chloride are provided below and are labeled Method A, Method B, and Method C. The resulting product is a chiral bishydroxamic acid ligand. The corresponding spectroscopic data for some of the ligands synthesized with these methods are provided, following each of the methods below.

Method A: A mixture of the acid chloride (40.4 mmol) and lithium iodide (16.2 g, 121.2 mmol) in CH$_2$Cl$_2$ (30 mL) was stirred at room temperature for 6 h and then cooled to −10° C. to be treated drop wise with a solution of VIII (5.85 g, 20.2 mmol) and diisopropylethylamine (8.9 mL, 52.2 mmol) in CH$_2$Cl$_2$ (25 mL). After stirring for 12 h at room temperature, 3 M aqueous HCl was added and stirring was continued for 30 min. The mixture was then extracted with methylene chloride (2×50 mL), dried (Na$_2$SO$_4$), and filtered. The filtrate was concentrated under reduced pressure and the residue was purified by flash column chromatography on silica gel to provide the chiral bishydroxamic acid ligand (I).

Example 7

This example provides spectroscopic data for (R,R)-N-{2-[(2,2-Dinaphthalen-1-ylacetyl)-hydroxyamino]-cyclohexyl}-N-hydroxy-2,2-dinaphthalen-1-ylacetamide (Ie) (3% yield). $^1$H NMR (400 MHz, CDCl$_3$) δ 8.96 (s, 2H), 7.98–7.14 (m, 28H), 6.40 (s, 2H), 4.40 (m 2H), 2.96–1.82 (m, 6H), 1.30 (m, 2H).

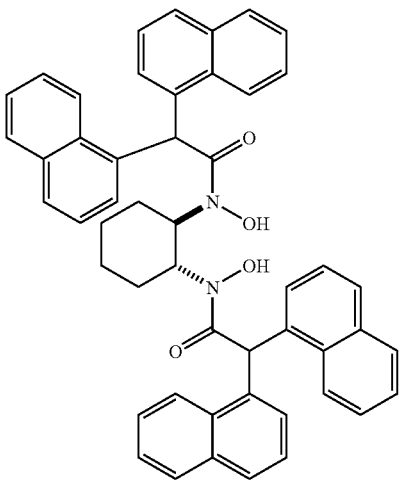

Example 8

This example provides spectroscopic data for (R,R)-N-(2-{[2,2-Bis-(3-methoxynaphthalen-2-yl)-acetyl]-hydroxyamino}-cyclohexyl)-N-hydroxy-2,2-bis-(3-methoxynaphthalen-2-yl)-acetamide (Ig) (Yield, 15%). $R_f$ 0.5 (EtOAc/hexanes, 1:1); $^1$H NMR (400 MHz, DMSO-$d_6$) δ 9.48 (s, 2H), 7.81 (d, J=8.2 Hz, 2H), 7.65 (d, J=8.1 Hz, 2H), 7.66 (d, J=6.6 Hz, 2H), 7.46–7.07 (m, 16H), 6.92–6.89 (m, 2H), 6.35 (s, 2H), 4.36–4.33 (m 2H), 3.78 (s, 6H), 3.62 (s, 6H), 1.86–1.83 (m, 2H), 1.66–1.64 (s, 2H), 1.52–1.50 (s, 2H), 1.20–1.18 (m, 2H); $^{13}$C NMR (125 MHz, DMSO-$d_6$) δ 174.4, 156.6, 156.4, 134.5, 134.4, 130.9, 130.0, 129.8, 129.0, 128.7, 128.5, 128.3, 127.3, 127.1, 127.0, 126.8, 124.6, 124.1, 106.3, 106.3, 57.4, 56.7, 56.4, 28.3, 25.0.

Ig

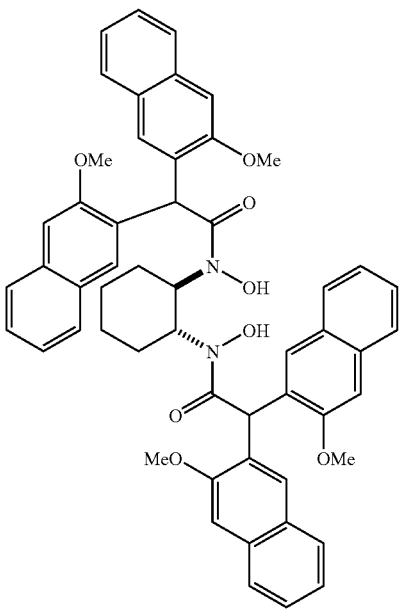

Example 9

This example provides spectroscopic data for Ip Yield, 55%; white solid: $R_f$ 0.42 (EtOAc/hexanes, 1:1); FTIR (KBr) $\upsilon_{max}$ 3150, 2940, 2863, 1609, 1572, 1501, 1449, 1451, 1406, 1316, 1254, 1175, 795, 714 cm$^{-1}$; $^1$H NMR (500 MHz, CDCl$_3$) δ 8.05 (s, 2H), 7.65 (d, J=7.8 Hz, 2H), 7.50 (t, J=7.2 Hz, 2H), 7.37 (d, J=7.8 Hz, 1H), 4.52–4.49 (m, 2H), 2.09–1.98 (m, 6H), 1.52–1.42 (m, 2H); $^{13}$C NMR (125 MHz, CDCl$_3$) δ 173.8 (C=O), 132.2 (C), 132.0 (C), 130.4 (CH), 127.8 (CH), 55.9 (CH), 28.2 (CH$_2$), 24.8 (CH$_2$).

Ip

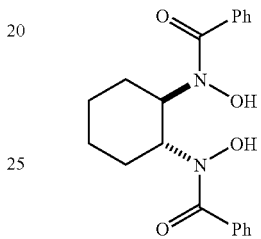

Method B: A general procedure for the preparation of chiral bishydroxamic acid ligands is herein provided. To a stirred solution of VIII (1 equiv) and DIEA (6 equiv) in CH$_2$Cl$_2$ was added acid chloride (3 equiv). After 24–72 h, the reaction mixture was concentrated under reduced pressure. To the residue, methanol followed by 0.5 M aqueous HCl was added. After stirring for 15–20 min the reaction mixture was extracted with CH$_2$Cl$_2$ (or EtOAc), washed with brine, dried (Na$_2$SO$_4$), and filtered. The filtrate was concentrated under reduced pressure and the residue was purified by flash column chromatography on silica gel to provide the chiral bis-hydroxamic acid ligand.

Example 10

This example provides spectroscopic data for (R,R)-N-[2-(Diphenylacetylhydroxyamino)-cyclohexyl]-N-hydroxy-2,2-diphenylacetamide (Ia) (Yield, 55%). White solid: $R_f$ 0.5 (EtOAc/hexanes, 3:7); FTIR (film) $\upsilon_{max}$ 3195, 3062, 3029, 2961, 2940, 2862, 1750, 1687, 1658, 1620, 1600, 1495, 1451, 1401, 1309, 1251, 1166, 1079, 1032, 909, 733, 699 cm$^{-1}$; $^1$H NMR (500 MHz, CDCl$_3$) δ 8.79 (s, 2H, OH), 7.31–7.26 (m, 5H), 7.21–7.18 (m, 5H), 7.16–7.05 (m, 10H), 5.49 (s, 2H), 4.49–4.48 (m 2H), 1.78–1.68 (m, 6H), 1.24–1.21 (m, 2H); $^{13}$C NMR (125 MHz, CDCl$_3$) δ 175.2 (C=O), 139.4 (C), 139.2 (C), 129.5 (CH), 128.9 (CH), 128.8 (CH), 128.7 (CH), 127.3 (CH), 127.1 (CH), 56.7 (CH), 53.4 (CH), 27.9 (CH$_2$), 24.6 (CH$_2$); HRMS-ESI calcd for C$_{34}$H$_{34}$O$_4$N$_2$Na [M+Na]$^+$ 557.2416, found 557.2438.

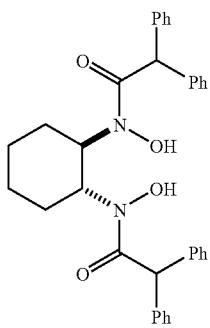

Ia

Example 11

This example provides spectroscopic data for (R,R)-N-{2-[(2,2-Di-naphthalen-2-ylacetyl)-hydroxyamino]-cyclohexyl}-N-hydroxy-2,2-dinaphthalen-2-ylacetamide (If) (31% yield): $R_f$ 0.6 (EtOAc/hexane, 1:2); FTIR (film) $\square_{max}$ 2937, 2862, 1605, 1507, 1406, 1264, 1235, 1168, 1017, 923, 854, 811, 741, 712 cm$^{-1}$; $^1$H NMR (400 MHz, CDCl$_3$) $\square$ 9.06 (s, 2H), 7.89–7.32 (m, 28H), 5.91 (s, 2H), 4.53–4.51 (m 2H), 1.86–1.76 (m, 6H), 1.31–1.21(m, 2H). $^{13}$C NMR (100 MHz, CDCl$_3$) n 175.1 (C=O), 136.5 (C), 133.4 (C), 133.3 (C), 132.5 (C), 132.4 (C), 128.3 (CH), 128.1 (CH), 127.97 (CH), 127.94 (CH), 127.61 (CH), 127.57 (CH), 127.19 (CH), 127.15 (CH), 127.0 (CH), 126.12 (CH), 126.09 (CH), 125.9 (CH), 56.6 (CH), 53.5 (CH), 27.8 (CH$_2$), 24.3 (CH$_2$).

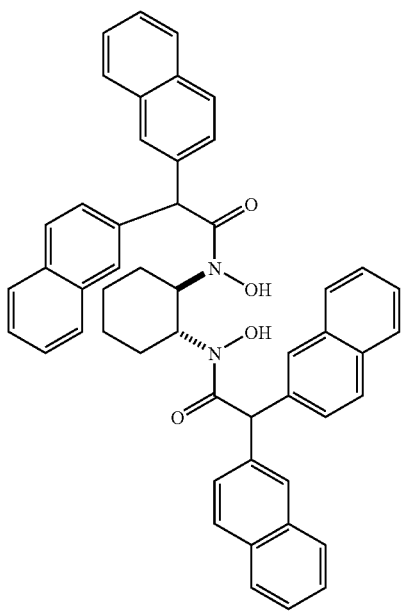

Example 12

This example provides spectroscopic data for (R,R)-N-(2-{[2,2-Bis-(4-tert-butylphenyl)-acetyl]-hydroxyamino}-cyclohexyl)-2,2-bis-(4-tert-butylphenyl)-N-hydroxyacetamide (Id) (Yield, 71%). White solid: $R_f$ 0.7 (EtOAc/hexanes, 3:7); FTIR (film) $\upsilon_{max}$ 3419, 2961, 2904, 2870, 1652, 1622, 1511, 1456, 1410, 1363, 1269, 1169, 819, 737, 668 cm$^{-1}$; $^1$H NMR (500 MHz, CDCl$_3$) δ 8.99 (s, 2H, OH), 7.32–7.28 (m, 6H), 7.21–7.15 (m, 12H), 5.53 (s, 2H), 4.32–4.30 (m 2H), 1.77–1.71 (m, 6H), 1.27–1.25 (m, 2H), 1.22 (s, 18H); $^{13}$C NMR (125 MHz, CDCl$_3$) δ 181.1 (C=O), 150.1 (C), 150.0 (C), 138.4 (C), 136.93 (C), 136.88 (C), 129.5 (CH), 128.9 (CH), 128.7 (CH), 126.1 (CH), 126.0 (CH), 126.0 (CH), 56.9 (CH), 53.5 (CH), 34.98 (C), 34.97 (C), 31.95 (CH$_3$), 31.92 (CH$_3$), 28.2 (CH$_2$), 24.9 (CH$_2$).

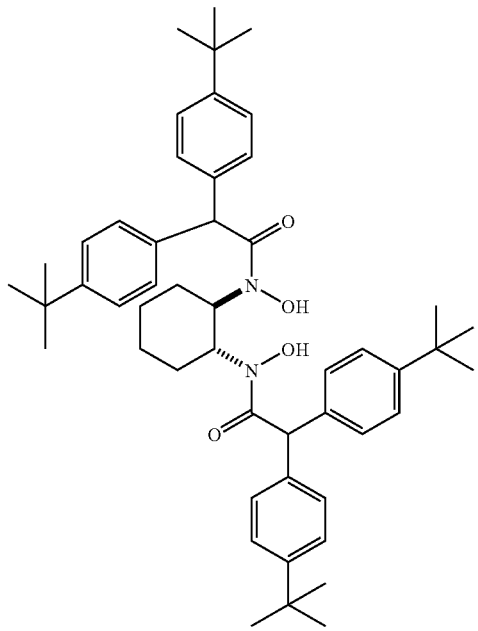

Id

Example 13

This example provides spectroscopic data for (R,R)-N-(2-{[2,2-Bis-(3,5-dimethylphenyl)-acetyl]-hydroxyamino}-cyclohexyl)-2,2-bis-(3,5-dimethylphenyl)-N-hydroxyacetamide (Im) (45% yield): $R_f$ 0.5 (EtOAc/hexane, 1:4); FTIR (film) $\upsilon_{max}$ 3172, 3007, 2919, 2861, 1621, 1602, 1452, 1404, 1309, 1264, 1233, 1166, 1132, 1037, 958, 897, 851, 823, 790, 770, 736, 710, 688, 660 cm$^{-1}$; $^1$H NMR (400 MHz, CDCl$_3$) δ 8.42 (s, 2H), 6.87–6.72 (m, 12H), 5.35 (s, 2H), 4.52–4.50 (m 2H), 2.27 (s, 12H), 2.14 (s, 12H), 1.89–1.77 (m, 6H), 1.26 (m, 2H); $^{13}$C NMR (100 MHz, CDCl$_3$) δ 175.0 (C=O), 139.2 (C), 139.0 (C), 137.9 (C), 137.5 (C), 128.6 (CH), 128.5 (CH), 126.8 (CH), 126.4 (CH), 56.5 (CH), 53.0 (CH), 27.7 (CH$_2$), 24.5, (CH$_2$), 21.4 (CH$_3$), 21.3 (CH$_3$); HRMS-ESI calcd for C$_{42}$H$_{50}$O$_4$N$_2$Na [M+Na]$^+$ 669.3668, found 669.3668.

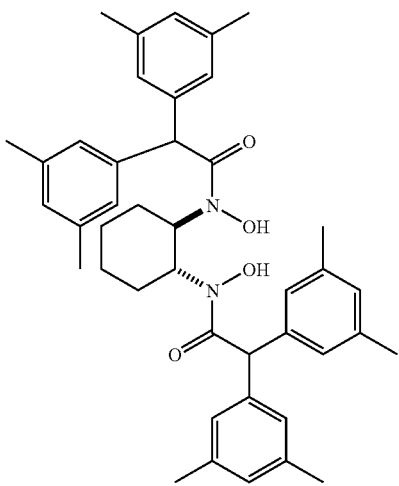

Example 14

This example provides spectroscopic data for (R,R)-N-(2-{[2,2-Bis-(3-methylphenyl)-acetyl]-hydroxyamino}-cyclohexyl)-2,2-bis-(3-methylphenyl)-N-hydroxyacetamide (In) (Yield, 50%). White solid: $^1$H NMR (400 MHz, CDCl$_3$) δ 8.80 (s, 2H), 7.21–7.18 (m, 2H), 7.06–6.84 (m, 14H), 5.43 (s, 2H), 4.42–4.50 (m 2H), 2.30 (s, 6H), 2.21 (s, 6H), 1.83–1.71 (m, 6H), 1.30–1.25 (m, 2H); HRMS-ESI calcd for C$_{38}$H$_{42}$O$_4$N$_2$Na [M+Na]$^+$ 613.3042, found 613.3029.

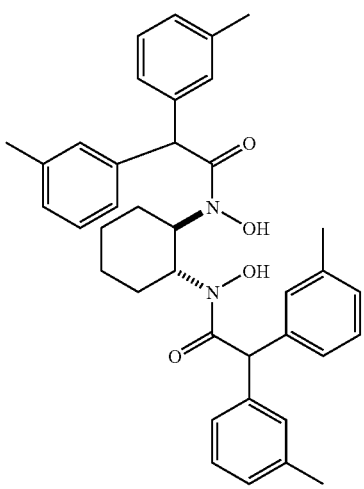

Example 15

This example provides spectroscopic data for (R,R)-2,2-Bis-biphenyl-3-yl-N-{2-[(2,2-bis-biphenyl-3-yl-acetyl)-hydroxyamino]-cyclohexyl}-N-hydroxyacetamide (Ib) (Yield, 55%). White solid; R$_f$ 0.4 (EtOAc/hexanes, 3:7); FTIR (film) υ$_{max}$ 3383, 3057, 3030, 2938, 2862, 1634, 1617, 1559, 1540, 1520, 1486, 1419, 1167, 1008, 911, 826, 764, 735, 696 cm$^{-1}$; $^1$H NMR (500 MHz, CDCl$_3$) δ 9.07 (s, 2H), 7.55–7.50 (m, 4H), 7.40–7.37 (m, 4H), 7.33–7.28 (m, 14H), 7.22–7.17 (m, 10H), 5.69 (s, 2H), 4.54–4.50 (m 2H), 1.85–1.76 (m, 6H), 1.27–1.25 (m, 2H); $^{13}$C NMR (125 MHz, CDCl$_3$) δ 175.1 (C=O), 140.9 (C), 140.4 (C), 141.2 (C), 140.0 (C), 138.4 (C), 138.3 (C), 129.9 (CH), 129.3 (CH), 129.0 (CH), 128.9 (CH), 127.6 (CH), 127.5 (CH), 127.4 (CH), 127.3 (CH), 127.1 (CH), 56.9 (CH), 52.9 (CH), 28.0 (CH$_2$), 24.6 (CH$_2$).

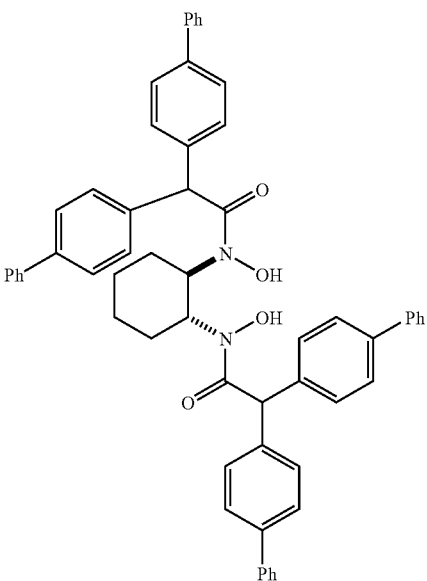

Example 16

This example provides spectroscopic data for (R,R)-2,2-Bis-biphenyl-3-yl-N-{2-[(2,2-bis-biphenyl-3-yl-acetyl)-hydroxyamino]-cyclohexyl}-N-hydroxy-acetamide (Ic) (Yield, 46%). White solid: R$_f$ 0.4 (EtOAc/hexanes, 3:7); FTIR (film) υ$_{max}$ 3420, 1623, 1599, 1478, 1455, 1419, 1170, 908, 755, 733, 699 cm$^{-1}$; $^1$H NMR (500 MHz, CDCl$_3$) δ 8.81 (s, 2H), 7.52–7.50 (m, 4H), 7.46–7.42 (m, 10H), 7.39–7.36 (m, 4H), 7.34–7.24 (m, 12H), 7.19 (d, J=7.5 Hz, 2H), 7.10 (d, J=8.0 Hz, 2H), 6.94–6.91 (m, 2H), 5.65 (s, 2H), 4.50–4.49 (m 2H), 1.80–1.74 (m, 6H), 1.26–1.24 (m, 2H); $^{13}$C NMR (125 MHz, CDCl$_3$) δ 175.0 (C=O), 141.7 (C), 141.6 (C), 141.2 (C), 141.0 (C), 138.9 (C), 139.6 (C), 129.2 (CH), 129.1 (CH), 129.0 (CH), 127.9 (CH), 127.73 (CH), 127.66 (CH), 127.6 (CH), 127.5 (CH), 127.44 (CH), 127.38 (CH), 126.2 (CH), 126.1 (CH), 56.7 (CH), 53.8 (CH), 28.1 (CH$_2$), 24.5 (CH$_2$).

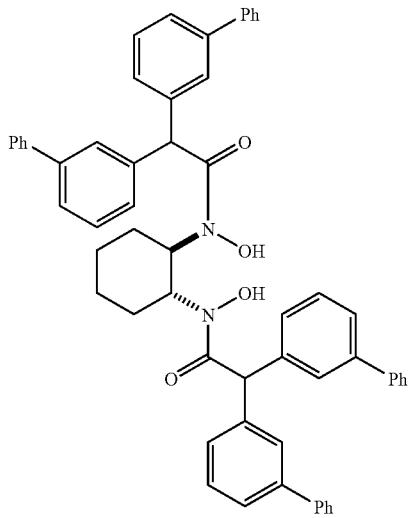

Example 17

This example provides spectroscopic data for Ik (Yield, 41%): white solid: $R_f$ 0.4 (EtOAc/hexanes, 3:7); FTIR (film) $\upsilon_{max}$ 3141, 2930, 2860, 1603 1470, 1169, 714, 668 cm$^{-1}$; $^1$H NMR (500 MHz, CDCl$_3$) δ 9.43 (s, 2H), 4.53–4.51 (m 2H), 3.21–3.16 (m, 2H), 1.90–1.82 (m, 6H), 1.61–1.52 (m, 6H), 1.43–1.25 9m 40H); $^{13}$C NMR (125 MHz, CDCl$_3$) δ 179.3 (C=O), 56.2 (CH), 36.3 (CH), 28.3 (CH$_2$), 26.8 (CH$_2$), 26.6 (CH$_2$), 24.9 (CH$_2$), 24.0 (CH$_2$), 23.93 (CH$_2$), 23.90 (CH$_2$), 23.87 (CH$_2$), 23.7 (CH$_2$), 23.61 (CH$_2$), 23.56 (CH$_2$), 22.8 (CH$_2$), 22.6 (CH$_2$).

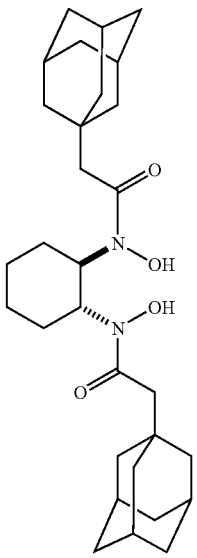

Example 18

This example provides spectroscopic data for (R,R)-2-Adamantan-1-yl-N-{2-[(2-adamantan-1-ylacetyl)-hydroxyamino]-cyclohexyl}-N-hydroxyacetamide (Ij) (Yield, 94%). White solid: $R_f$ 0.68 (EtOAc/hexanes, 3:7); FTIR (film) $\upsilon_{max}$ 3151, 2902, 2848, 1602, 1450, 1172, 909, 733 cm$^{-1}$; $^1$H NMR (400 MHz, CDCl$_3$) δ 8.38 (s, 2H, OH), 4.44–4.39 (m 2H), 2.59 (d, J=12.7 Hz, 2H), 1.90 (d, J=12.7 Hz, 2H), 1.86–1.80 (m, 6H), 1.70–1.57 (m, 28H), 1.40–1.30 (m, 2H); $^{13}$C NMR (100 MHz, CDCl$_3$) δ 175.0 (C=O), 55.3 (CH), 46.0 (CH$_2$), 42.8 (CH$_2$), 37.0 (CH$_2$), 33.8 (C), 28.9 (CH), 28.4 (CH$_2$), 24.8 (CH$_2$).

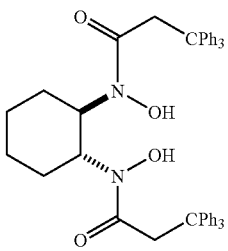

Example 19

This example provides spectroscopic data for (R,R)-N-Hydroxy-N-{2-[hydroxy-(3,3,3-triphenylpropionyl)-amino]-cyclohexyl}-3,3,3-triphenylpropionamide (Io) (Yield, 72%). White solid: $R_f$ 0.63 (EtOAc/hexanes, 1:3); FTIR (film) $\upsilon_{max}$ 3150, 2938, 2859, 1616, 1493, 1446, 1419, 1170, 769, 700 cm$^{-1}$; $^1$H NMR (400 MHz, CDCl$_3$) δ 8.26 (s, 2H), 7.28–7.17(m, 30H), 4.19 (d, J=16.1 Hz, 2H), 3.94–3.92 (m, 2H), 3.55 (d, J=16.1 Hz, 2H), 1.68–1.65 (m, 2H), 1.50–1.38 (m, 4H), 1.12–1.07 (m, 2H); $^{13}$C NMR (100 MHz, CDCl$_3$) δ 173.6 (C=O), 147.2 (C), 129.6 (CH), 127.8 (CH), 126.3 (CH), 56.2 (C), 55.2 (CH), 42.5 (CH$_2$), 27.5 (CH$_2$), 24.6 (CH$_2$); HRMS-ESI calcd for C$_{48}$H$_{46}$O$_4$N$_2$Na [M+Na]$^+$ 737.3355, found 737.3379.

Method C: To a stirred solution of VIII (1 equiv) and DIEA (6 equiv) in CH$_2$Cl$_2$ was added acid chloride. After 48 h, the reaction mixture was concentrated under reduced pressure and methanol followed by 0.5 M aqueous HCl was added to the residue. After stirring for 15–20 min the reaction mixture was extracted with CH$_2$Cl$_2$, washed with brine, dried (Na$_2$SO$_4$), and filtered. The filtrate was concentrated under reduced pressure and the residue was purified by flash column chromatography on silica gel to provide monohydroxamic acid. To a stirred solution of monohydroxamic acid in CH$_2$Cl$_2$ was added freshly prepared acid chloride and DIEA. After 48 h, the reaction mixture was poured into saturated aqueous NH$_4$Cl solution and extracted with EtOAc, washed with brine, dried (Na$_2$SO$_4$), and filtered. The filtrate was concentrated under reduced pressure and the residue was purified by flash column chromatography on silica gel to provide the chiral bishydroxamic acid ligand.

Example 20

This example provides spectroscopic data for (R,R)-2,2-Dicyclohexyl-N-{2-[(2,2-dicyclohexyl-acetyl)-hydroxy-amino]-cyclohexyl}-N-hydroxy-acetamide (IL) (Yield, 28%). White solid: R$_f$ 0.61 (EtOAc/hexanes, 3:7); FTIR (film) $\upsilon_{max}$ 3149, 2930, 2849, 1616, 1577, 1445, 1374, 1177 cm$^{-1}$; $^1$H NMR (500 MHz, CDCl$_3$) δ 9.00 (s, 2H, OH), 4.57–4.50 (m, 2H), 2.96 (dd, J=9.0, 5.0 Hz, 2H), 1.89–0.89 (series of m, 52H); $^{13}$C NMR (125 MHz, CDCl$_3$) δ 178.9 (C=O), 57.8 (CH), 51.2 (CH), 38.9 (CH$_2$), 36.9 (CH$_2$), 32.3 (CH$_2$), 32.1 (CH$_2$), 31.2 (CH$_2$), 29.5 (CH$_2$), 29.3 (CH$_2$), 27.6 (CH$_2$), 27.5 (CH$_2$), 27.2 (CH$_2$), 27.14 (CH$_2$), 27.10 (CH$_2$), 25.3 (CH$_2$); HRMS-ESI calcd for C$_{34}$H$_{58}$O$_4$N$_2$Na [M+Na]$^+$ 581.4294, found 581.4294.

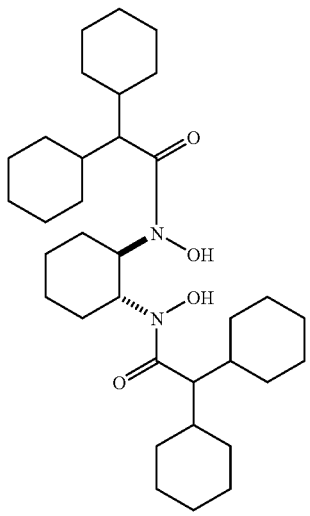

IL

Example 21

The general procedure for the preparation of the alcohol (a precursor to the acid chloride used in the preparation of the acid chloride) is shown below. The R' substituent can be selected from the group consisting of alkyl, cycloalkyl, alkoxy, alkylamino, heterocyclyl, aryl, heteroaryl, and arylalkyl.

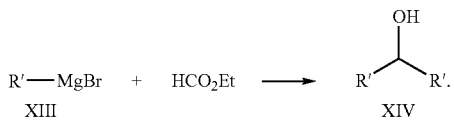

To a stirred suspension of magnesium (1.1 equiv) in THF (10 mL), under an atmosphere of argon at room temperature, was added a small crystal of iodine, the resulting mixture was heated at reflux. To this refluxing solution, a small portion of aryl bromide (XIII) (~5% of the total amount: 1 equiv) was added and the heating was continued. After 5 minutes, the remaining aryl bromide was added and was heated at reflux in an oil bath for 1–2 h according to substrate. The oil bath was removed, ethyl formate was added drop wise over 5 min to the hot reaction mixture, and then stirred for 1–2 h at room temperature. The reaction mixture was poured into saturated aqueous NH$_4$Cl. After stirring for 30 minutes, the biphasic mixture was extracted with EtOAc (3 times) and the combined organic extracts washed with brine (20 mL), dried (Na$_2$SO$_4$), filtered and concentrated under reduced pressure to provide crude alcohol XIV, which was purified by column chromatography on silica gel or recrystalization according to the substrate.

Example 22

This example provides spectroscopic data for bis-(3-methoxynaphthalen-2-yl)-methanol (Yield, 74%). $^1$H NMR (500 MHz, CDCl$_3$) δ 7.74 (d, J=8.0 Hz, 2H), 7.69 (d, J=8.0 Hz, 2H), 7.66 (s, 2H), 7.46–7.41 (m, 2H), 7.32–7.29 (m, 2H), 7.17 (s, 2H), 6.60 (s, 1H), 3.93 (s, 6H), 3.50 (brs, 1H).

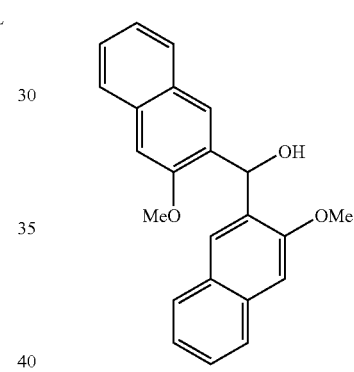

Example 23

This example provides spectroscopic data for bis-(4-tert-butylphenyl)-methanol Yield, 90%; $^1$H NMR (400 MHz, CDCl$_3$) δ 7.37 (d, J=8.6 Hz, 4H), 7.34 (d, J=8.6 Hz, 4H), 5.83 (s, 1H), 2.16 (br s, 1H), 1.34 (s, 18H).

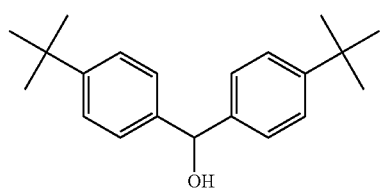

Example 24

This example provides spectroscopic data for bis-biphenyl-4-yl-methanol (Yield, 84%). $^1$H NMR (500 MHz, CDCl$_3$) 7.62–7.59 (m, 8H), 7.52 (d, J=8.2 Hz, 4H), 7.47–7.44 (m, 4H), 7.32–7.29 (m, 4H), 5.97 (s, 1H), 2.31 (brs, 1H).

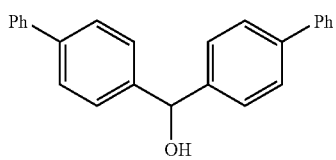

Example 25

This example provides spectroscopic data for bis-biphenyl-4-yl-methanol: Yield, 81%; $^1$H NMR (500 MHz, CDCl$_3$) 7.70 (s, 2H), 7.62–7.60 (m, 4H), 7.48–7.47 (m, 2H), 7.46–7.43 (m, 8H), 7.38–7.37 (m, 2H), 5.32 (s, 2H);

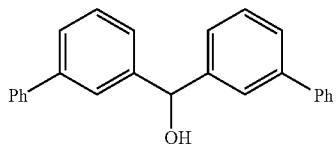

Example 26

This example provides spectroscopic data for bis-(naphthalen-2-yl)-methanol $^1$H NMR (400 MHz, CDCl$_3$) δ 7.95 (s, 2H), 7.86–7.79 (m, 6H), 7.50–7.46 (m, 6H), 6.16 (s, 1H), 2.53 (s, 1H).

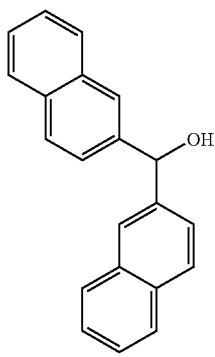

Example 27

This example provides spectroscopic data for bis-(naphthalen-1-yl)-methanol: $^1$H NMR (400 MHz, CDCl$_3$) δ 7.89 (d, J=8.4 Hz, 2H), 7.91 (d, J=8.0 Hz, 2H), 7.82 (d, J=7.8 Hz, 2H), 7.53–7.37 (m, 8H), 7.20 (s, 1H), 2.73 (s, 1H).

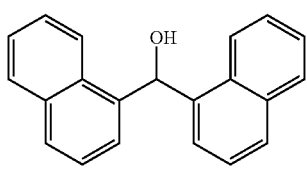

Example 28

This example provides spectroscopic data for bis-(3,5-dimethyl-phenyl)-methanol: (81% yield): $^1$H NMR (400 MHz, CDCl$_3$) δ 7.00 (s, 4H), 6.90 (s, 2H), 5.70 (d, J=3.2 Hz, 1H), 2.30 (s, 12H), 2.12 (d, J=3.4 Hz, 1H).

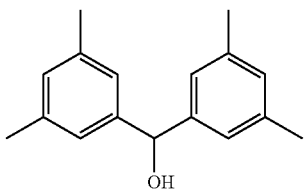

Example 29

The general procedure for the reduction of the Alcohol is shown below.

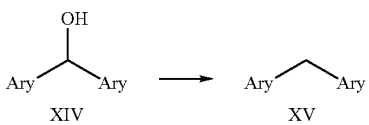

To a stirred suspension of NaI (6 equiv) in MeCN, under an atmosphere of nitrogen at room temperature, was added trimethylsilylchloride (6 equiv). After stirring for 20 min, the reaction mixture was cooled to 0° C., a solution of alcohol XIV (1 equiv) in CH$_2$Cl$_2$ and MeCN (1:1 mixture), was added over 1 h. After stirring for a further 30 min. at the same temperature, the reaction mixture was allowed to warm to room temperature over 5 min. and then immediately cooled to 0° C., poured into aqueous NaOH (4 equiv), additional NaOH solution was added to adjust pH of aqueous layer to 7. The biphasic mixture was extracted with EtOAc (2 times) and the organic phase was washed with saturated aqueous Na$_2$S$_2$O$_3$ to completely remove any color of iodine. The aqueous portion was extracted with small amount EtOAc and he combined organic extracts were then dried (Na$_2$SO$_4$), filtered and concentrated under reduced pressure. The residue was purified by the flash column chromatography on silica gel or recrystalization to provide the desired compound (XV).

Example 30

This example provides spectroscopic data for bis-(3-methoxynaphthalen-2-yl)-methane: Yield, 89%; $^1$H NMR (500 MHz, CDCl$_3$) δ 7.69 (d, J=8.2 Hz, 2H), 7.58 (d, J=8.2 Hz, 2H), 7.39 (s, 2H), 7.36–7.33 (m, 2H), 7.26–7.23 (m, 2H), 7.10 (s, 2H), 4.21 (s, 2H), 3.87 (s, 6H).

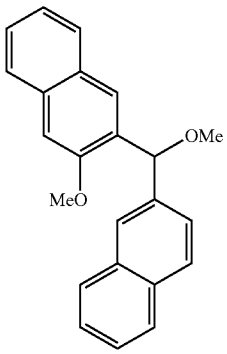

Example 31

This example provides spectroscopic data for bis-(4-tert-butyl-phenyl)-methanol: Yield, 90%; $^1$H NMR (500 MHz, CDCl$_3$) δ 7.27 (d, J=8.0 Hz, 4H), 7.10 (d, J=8.0 Hz, 4H), 3.89 (s, 2H), 1.26 (s, 18H).

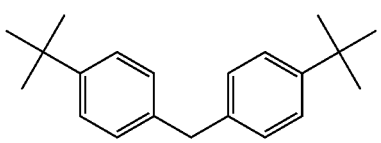

Example 32

This example provides spectroscopic data for bis-biphenyl-4-yl-methane: Yield, 92%; $^1$H NMR (500 MHz, CDCl$_3$) δ 7.56–7.54 (m, 4H), 7.41–7.40 (m, 4H), 7.47–7.44 (m, 4H), 7.38–7.27 (m, 6H), 4.04 (s, 2H).

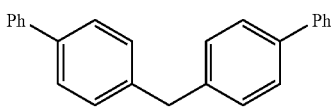

Example 33

This example provides spectroscopic data for bis-biphenyl-4-yl-methane Yield, 64%; FTIR (film) υ$_{max}$ cm$^{-1}$; $^1$H NMR (500 MHz, CDCl$_3$) δ 7.56–7.54 (m, 4H), 7.44–7.38 (m, 8H), 7.34–7.29 (m, 4H), 7.20–7.19 (m, 2H), 4.09 (s, 2H).

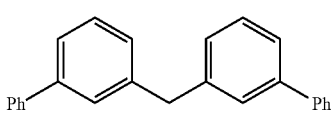

Example 34

This example provides spectroscopic data for bis-(naphthalen-2-yl)-methane: 66% yield; $^1$H NMR (400 MHz, CDCl$_3$) δ 7.87–7.81 (m, 6H), 7.73 (s, 2H), 7.53–7.46 (m, 4H), 7.39 (dd, J=8.4 Hz, 1.6 Hz, 2H), 4.35 (s, 2H).

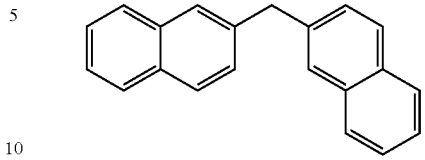

Example 35

This example provides spectroscopic data for bis-(naphthalen-1-yl)-methane: 67% yield; $^1$H NMR (400 MHz, CDCl$_3$) δ 8.07 (d, J=8.0 Hz, 2H), 7.94 (d, J=7.6 Hz, 2H), 7.80 (d, J=8.4 Hz, 2H), 7.57–7.50 (m, 4H), 7.36 (t, J=8.0 Hz, 2H), 7.11 (d, J=6.8 Hz, 2H), 4.92 (s, 2H).

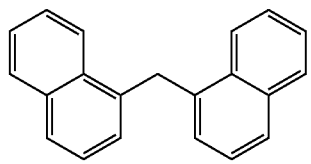

Example 36

This example provides spectroscopic data for bis-(3,5-dimethylphenyl)-methane: 82% yield; $^1$H NMR (400 MHz, CDCl$_3$) δ 6.83 (s, 2H), 6.81 (s, 4H), 3.82 (s, 2H), 2.27 (s, 12H).

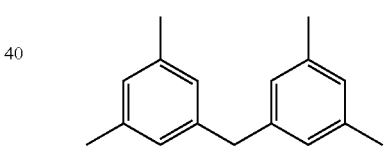

Example 37

The general procedure for preparation of the carboxylic acid is shown below.

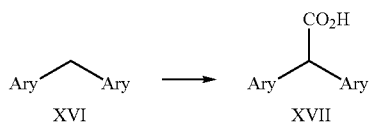

To a stirred suspension of diarylmethane (XVI) (1 equiv) in THF, under an atmosphere of argon, at room temperature was added n-butyl lithium (1.3 equiv). After 1 h, anhydrous CO$_2$ was bubbled through the reaction mixture and stirred for additional 1 h. Once all the alkyl lithium species were consumed, the reaction mixture was concentrated under reduced pressure and aqueous NaOH (10–15 equiv) was added. The aqueous solution was washed with ether and separated, acidified with 1 M HCl to pH 2–3 which was extracted with EtOAc (3 times). The combined organic extracts were then dried (Na$_2$SO$_4$), filtered and concentrated under reduced pressure. The residue was purified by recrystalization, to provide carboxylic acid XVII.

Example 38

This example provides spectroscopic data for bis-(3-methoxy-naphthalen-2-yl)-acetic acid: Yield, 83%; $^1$H NMR (500 MHz, DMSO-d$_6$) δ 7.86 (d, J=8.1 Hz, 2H), 7.73 (d, J=8.2 Hz, 2H), 7.48–7.42 (m, 6H), 7.32–7.30 (m, 2H), 5.68 (s, 1H), 3.90 (s, 6H).

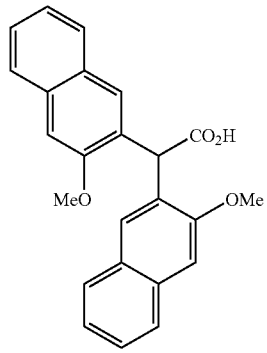

Example 39

This example provides spectroscopic data for bis-(4-tert-butylphenyl)-acetic acid: Yield, 63%; $^1$H NMR (500 MHz, DMSO-d$_6$+1 M HCl) δ 7.19–7.17 (m, 4H), 7.10–7.07 (m, 4H), 4.78 (s, 1H), 1.11 (s, 9H), 1.09 (s, 9H).

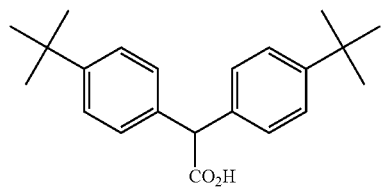

Example 40

This example provides spectroscopic data for bis-biphenyl-4-yl-acetic acid: Yield, 87%; $^1$H NMR (500 MHz, DMSO-d$_6$) δ 7.54–7.52 (m, 8H), 7.34–7.33 (m, 8H), 7.26–7.25 (m, 2H), 5.07 (s, 1H).

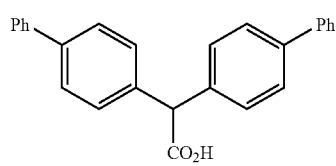

Example 41

This example provides spectroscopic data for bis-biphenyl-3-yl-acetic acid: Yield, 83%; $^1$H NMR (500 MHz, DMSO-d$_6$) δ 7.56–7.54 (m, 2H), 7.51–7.33–7.49 (m, 4H), 7.37–7.35 (m, 2H), 7.31–7.24 (m, 10H), 5.15 (s, 1H).

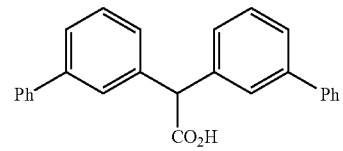

Example 42

This example provides spectroscopic data for bis-(naphthalen-2-yl)-acetic acid: 72% yield; $^1$H NMR (400 MHz, DMSO-d$_6$) δ 12.91 (bs, 1H), 7.90–7.88 (m, 8H), 7.54–7.48 (m, 6H), 5.45 (s, 1H).

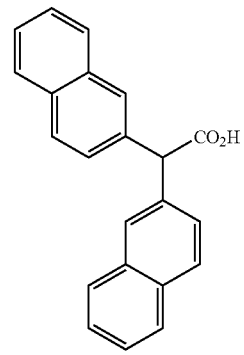

Example 43

This example provides spectroscopic data for bis-(naphthalen-1-yl)-acetic acid (57% yield); $^1$H NMR (400 MHz, DMSO-d$_6$) δ 13.05 (bs, 1H), 8.06–8.02 (m, 4H), 7.93 (d, J=8.2 Hz, 2H) 7.61–7.47 (m, 6H), 7.22 (d, J=7.1 Hz, 2H), 6.54 (s, 1H).

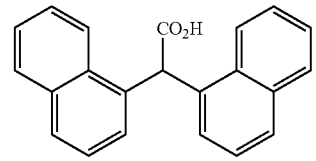

Example 44

This example provides spectroscopic data for bis-(3,5-dimethyl-phenyl)-acetic acid (58% yield); $^1$H NMR (400 MHz, DMSO-d$_6$) δ 12.57 (bs, 1H), 6.90 (s, 4H), 6.86 (s, 2H), 4.85 (s, 1H), 2.23 (s, 12H).

Example 45

The general Procedure for asymmetric epoxidation of allylic alcohols in the presence of VO(OPr$^i$)$_3$ and hydroxamic acid ligand is shown below.

To a solution of hydroxamic acid (0.02 equiv) in toluene was added VO(OPr$^i$)$_3$ (0.01 equiv), and the mixture was stirred for 1 h at room temperature. The resulting solution was cooled to 0° C., 70% aqueous tert-butylhydroperoxide (TBHP) (1.5 equiv) and allyl alcohol Xb (1 equiv) were added and stirring was continued at the same temperature for several hours at the same temperature monitoring the progress of the reaction by TLC. When the epoxidation was complete according to TLC, a saturated aqueous Na$_2$SO$_3$ was added and the mixture was warmed to room temperature over a period of 15 min, extracted with Et$_2$O, dried (Na$_2$SO$_4$) and concentrated under reduced pressure. The remaining residue was purified by flash column chromatography on silica gel to provide epoxy alcohol. The enantiomeric excess of the epoxy alcohol XIIa was determined by HPLC using chiral OD-H column (hexanes/2-propanol, 95:5), 0.5 mL/min; major enantiomer t$_r$=13.9 min, minor enatiomer t$_r$=12.0 min.

The invention claimed is:

1. A method of performing a catalytic asymmetric epoxidation comprising:
reacting an alkene or cyclic alkene with catalytic amounts of a chiral bishydroxamic acid ligand and a metal, in the presence of an oxidation reagent, to produce a chiral epoxide, where the chiral bishydroxamic acid ligand has a structure I:

where:
R$^1$, R$^2$, R$^3$, R$^4$, R$^5$, and R$^6$ are each independently selected from the group consisting of hydrogen, alkyl, cycloalkyl, alkoxy, alkylamino, heterocyclyl, aryl, heteroaryl, and arylalkyl;
or where R$^1$ and R$^2$, together with the atom to which they are attached, form a substituted or unsubstituted ring selected from the group consisting of cycloalkyl, heterocyclyl, and aryl;
or where R$^4$ and R$^5$, together with the atom to which they are attached, form a substituted or unsubstituted ring selected from the group consisting of cycloalkyl, heterocyclyl, and aryl;
R$^7$, R$^8$, R$^9$, and R$^{10}$ are each independently selected from the group consisting of hydrogen, alkyl, cycloalkyl, alkoxy, alkylamino, heterocyclyl, aryl, heteroaryl, and arylalkyl;
or where R$^7$ and R$^9$, together with the atoms to which they are attached, form a substituted or non-substituted ring selected from the group consisting of cycloalkyl and heterocyclyl;
-Z- is selected from the group consisting of —C(O)— and —S(O)$_2$—.

2. The method of claim 1, where the metal is selected from the group consisting of vanadium (IV), vanadium (V), molybdenum (IV), molybdenum (V), and molybdenum (VI).

3. The method of claim 2, where the metal is selected from the group consisting of vanadium (IV) and vanadium (V).

4. The method of claim 2, where the metal is selected from the group consisting of molybdenum (IV), molybendum (V), and molybendum (VI).

5. The method of claim 1, where the oxidation reagent is an organic hydroperoxide with the following structure (II):

$$R^{11}—O—OH \qquad II$$

where, R$^{11}$ is selected from the group consisting of alkyl, cycloalkyl, aryl, heteroaryl, and heterocyclyl.

6. The method of claim 1, where R$^1$, R$^2$, R$^3$, R$^4$, R$^5$, and R$^6$ are each independently selected from the group consisting of hydrogen, alkyl, alkyoxy, and alkylamino.

7. The method of claim 1, where R$^1$, R$^2$, R$^3$, R$^4$, R$^5$, and R$^6$ are each independently selected from the group consisting of cycloalkyl and heterocyclyl.

8. The method of claim 1, where R$^1$, R$^2$, R$^3$, R$^4$, R$^5$, and R$^6$ are each independently selected from the group consisting of aryl, arylalkyl, heteroaryl, and halogen.

9. The method of claim 1, where:
R$^1$ and R$^2$, together with the atom to which they are attached, form a substituted or unsubstituted ring;
R$^4$ and R$^5$, together with the atom to which they are attached, form a substituted or unsubstituted ring; and
the ring formed by R$^1$ and R$^2$ is identical to the ring formed by R$^4$ and R$^5$.

10. The method of claim 1, where R$^7$, R$^8$, R$^9$, and R$^{10}$ are each independently selected from the group consisting of hydrogen, alkyl, alkyoxy, and alkylamino.

11. The method of claim 1, where R$^7$, R$^8$, R$^9$, and R$^{10}$ are each independently selected from the group consisting of cycloalkyl and heterocyclyl.

12. The method of claim 1, where R$^7$, R$^8$, R$^9$, and R$^{10}$ are each independently selected from the group consisting of aryl, arylalkyl, and heteroaryl.

13. The method of claim 1, where R$^7$ and R$^9$, together with the atoms to which they are attached, form a ring.

14. The method of claim 13, where R$^8$ and R$^{10}$ are identical.

15. The method of claim 11, where $R^7$ and $R^9$, together with the atoms to which they are attached, form a ring.

16. The method of claim 15, where $R^8$ and $R^{10}$ are identical.

17. The method of claim 1, where:
$R^1$ and $R^2$ are aryl groups;
$R^3$ is hydrogen;
$R^4$ and $R^5$ are aryl groups; and
$R^6$ is hydrogen.

18. The method of claim 17, where:
$R^1$ and $R^2$ are identical; and
$R^4$ and $R^5$ are identical.

19. The method of claim 18, where $R_1$, $R^2$, $R^4$, and $R^5$ are identical.

20. The method of claim 1, where the chiral bishydroxamic acid ligand (I) is selected from the group consisting of:

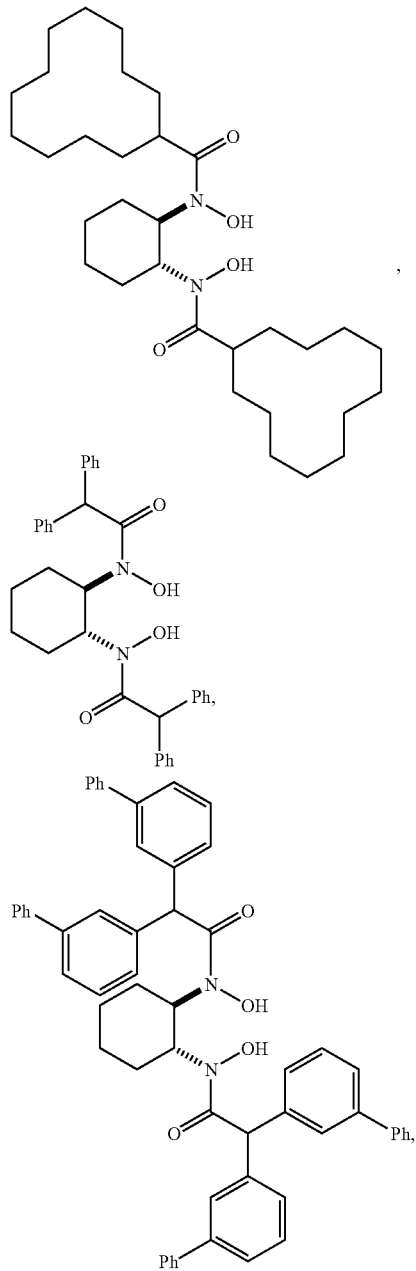

-continued

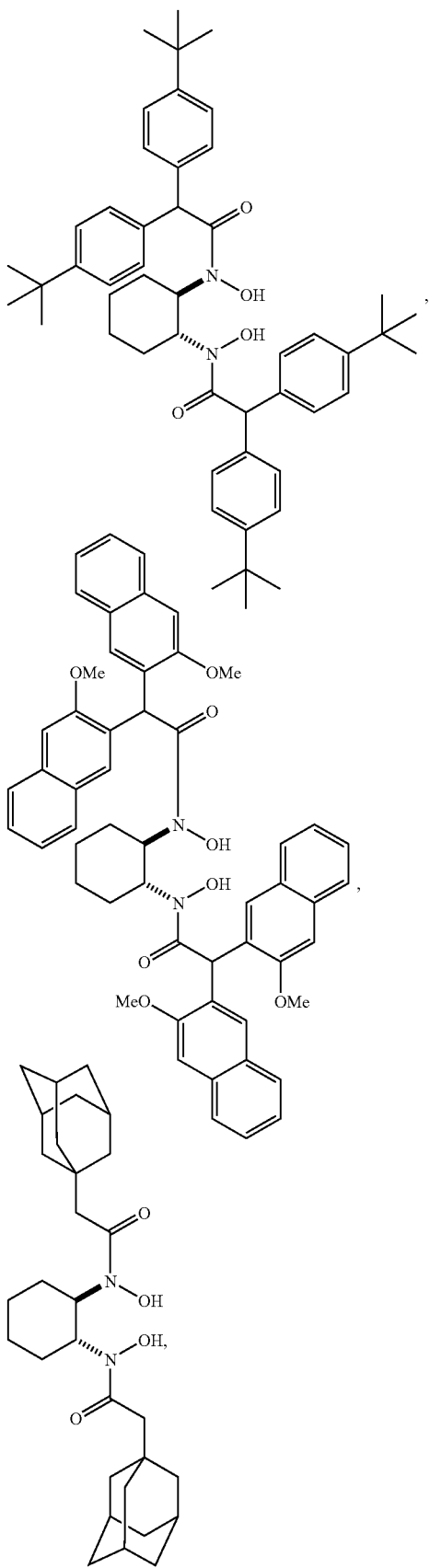

61
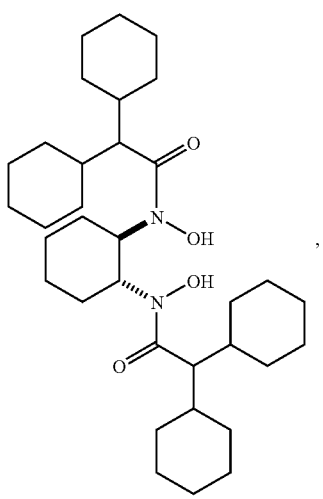
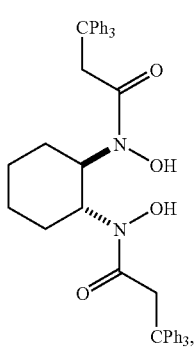
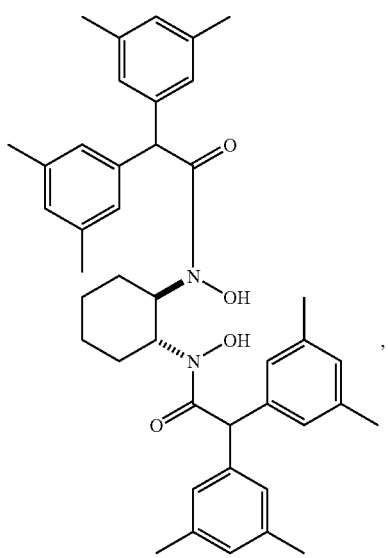
62
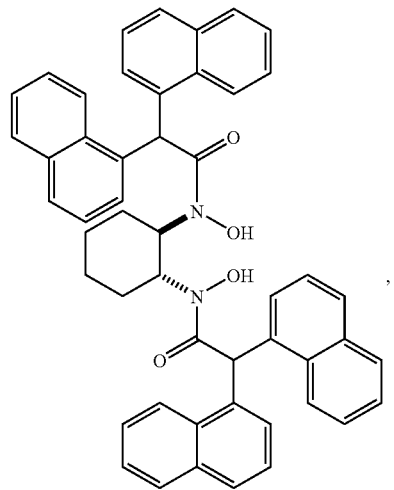
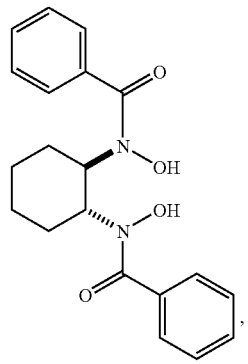 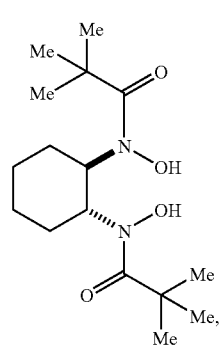
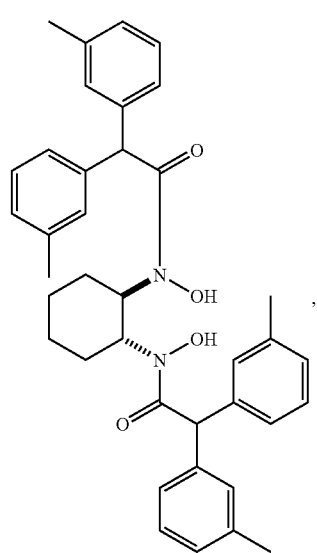

-continued

21. The method of claim 2, where the metal is selected from the group consisting of VO(OPr)$^i$, VO(acac)$_2$, VO(OEt)$_3$, and MoO$_2$(acac)$_2$.

22. The method of claim 5, where the organic hydroperoxide is selected from the group consisting of tert-butyl hydroperoxide and cumene hydroperoxide.

23. The method of claim 5, where the organic hydroperoxide is tert-butyl hydroperoxide.

24. The method of claim 5, where the organic hydroperoxide is cumene hydroperoxide.

25. The method of claim 2, where the oxidation reagent is selected from the group consisting of tert-butyl hydroperoxide and cumene hydroperoxide.

26. The method of claim 2, where the oxidation reagent is tert-butyl hydroperoxide.

27. The method of claim 2, where the oxidation reagent is cumene hydroperoxide.

28. The method of claim 1, where the oxidation reagent is hydrogen peroxide.

29. The method of claim 2, where the oxidation reagent is hydrogen peroxide.

30. A method of performing a catalytic asymmetric epoxidation comprising:

reacting an alkene or cyclic alkene with catalytic amounts of a chiral bishydroxamic acid ligand and a metal, in the presence of an oxidation reagent, to produce a chiral epoxide, where the chiral bishydroxamic acid ligand is selected from the following formulae:

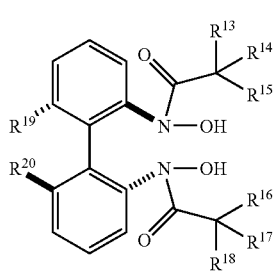

Ib′

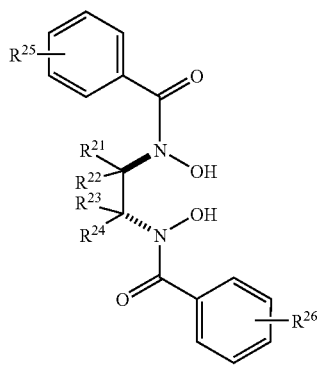

Ic′ where:

$R^{13}$, $R^{14}$, $R^{15}$, $R^{16}$, $R^{17}$, and $R^{18}$ are each independently selected from the group consisting of hydrogen, alkyl, cycloalkyl, alkoxy, alkylamino, heterocyclyl, aryl, heteroaryl, and arylalkyl;

$R^{19}$ and $R^{20}$ are each independently selected from the group consisting of hydrogen, halogen, alkyl, cycloalkyl, alkoxy, alkylamino, heterocyclyl, aryl, heteroaryl, and arylalkyl;

$R^{21}$, $R^{22}$, $R^{23}$, and $R^{24}$ are each independently selected from the group consisting of hydrogen, alkyl, cycloalkyl, alkoxy, alkylamino, heterocyclyl, aryl, heteroaryl, and arylalkyl;

$R^{25}$ and $R^{26}$ are each independently selected from the group consisting of hydrogen, halogen, alkyl, cycloalkyl, alkoxy, alkylamino, heterocyclyl, aryl, heteroaryl, and arylalkyl.

31. The method of claim 1, where the alkene is of the formula (X):

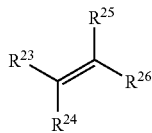

where:
R$^{23}$, R$^{24}$, R$^{25}$, and R$^{26}$ are each independently selected from the group consisting of hydrogen, halogen, alkyl, cycloalkyl, alkoxy, alkylamino, heterocyclyl, aryl, heteroaryl, and arylalkyl.

32. The method of claim 1, where the alkene is a cyclic alkene of the formula (Xa):

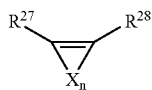

where:
R$^{27}$ and R$^{28}$ are each independently selected from the group consisting of hydrogen, alkyl, cycloalkyl, alkoxy, alkylamino, heterocyclyl, aryl, aralklyl, heteroaryl, halogen, and alkene;
n is 1, 2, 3, 4, 5, or 6;
each X is independently selected from the group consisting of CR'R", —NR'—, and —O—;
R' and R" are each independently selected from the group consisting of hydrogen, alkyl, cycloalkyl, alkoxy, alkylamino, heterocyclyl, aryl, aralklyl, heteroaryl, and halogen.

33. The method of claim 31, where the chiral oxidation product is of the formula (Xb):

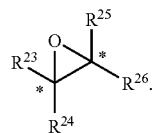

34. The method of claim 32, where the chiral oxidation product is of the formula (Xc):

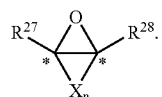

35. The method of claim 1, where the reacting step is carried out in a solvent.

36. The method of claim 35, where the reacting step is carried out in a solvent selected from the group consisting of methylene chloride, toluene, chloroform, and ethyl acetate.

37. The method of claim 1, where the reacting step is carried out at a temperature of about −20 to about 25° C.

38. The method of claim 1, where the reaction is carried out with about 0.001 to about 0.1 equivalents of the chiral bishydroxamic acid ligand (I).

39. The method of claim 1, where the reaction is carried out with about 0.005 to about 0.05 equivalents of metal.

* * * * *

UNITED STATES PATENT AND TRADEMARK OFFICE
CERTIFICATE OF CORRECTION

PATENT NO. : 7,202,371 B2  Page 1 of 1
APPLICATION NO. : 10/762028
DATED : April 10, 2007
INVENTOR(S) : Hisashi Yamamoto et al.

It is certified that error appears in the above-identified patent and that said Letters Patent is hereby corrected as shown below:

In the Claims

Column 59, line 13, delete "$R_1$" and susbtitute --$R^1$-- in its place.

Column 63, line 55, delete "$VO(OPr)^i$" and substitute --$VO(OPr^i)_3$-- in its place.

Signed and Sealed this

Tenth Day of July, 2007

JON W. DUDAS
*Director of the United States Patent and Trademark Office*